US010250301B2

(12) United States Patent
Pagani

(10) Patent No.: US 10,250,301 B2
(45) Date of Patent: Apr. 2, 2019

(54) NETWORK OF ELECTRONIC DEVICES ASSEMBLED ON A FLEXIBLE SUPPORT AND COMMUNICATION METHOD

(71) Applicant: STMicroelectronics S.r.l., Agrate Brianza (IT)

(72) Inventor: Alberto Pagani, Nova Milanese (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 35 days.

(21) Appl. No.: 15/375,761

(22) Filed: Dec. 12, 2016

(65) Prior Publication Data

US 2017/0093024 A1 Mar. 30, 2017

Related U.S. Application Data

(63) Continuation of application No. 13/905,342, filed on May 30, 2013, now Pat. No. 9,520,921.

(30) Foreign Application Priority Data

May 31, 2012 (IT) ............................. TO2012A0477

(51) Int. Cl.
*H04B 5/00* (2006.01)
*H02J 50/12* (2016.01)
(Continued)

(52) U.S. Cl.
CPC ........... *H04B 5/0075* (2013.01); *H01F 38/14* (2013.01); *H01L 23/5387* (2013.01);
(Continued)

(58) Field of Classification Search
CPC ......... H04B 5/0075; H01F 5/00; H01F 38/14; G01R 31/02; H01L 29/82; H01L 23/5387
See application file for complete search history.

(56) References Cited

U.S. PATENT DOCUMENTS 6,473,308 B2 10/2002 Forthun
6,788,262 B1 * 9/2004 Adams ................... H01Q 1/085
343/718

(Continued)

FOREIGN PATENT DOCUMENTS

WO WO-2005055390 A1 6/2005
WO WO-2005106901 A2 11/2005
(Continued)

OTHER PUBLICATIONS

IT Search Report and Written Opinion for IT Appl. No. TO2012A000477 dated Apr. 11, 2013 (11 pages).
(Continued)

*Primary Examiner* — Md K Talukder
(74) *Attorney, Agent, or Firm* — Crowe & Dunlevy

(57) ABSTRACT

Disclosed herein is an article including a garment, with a network formed on the garment. The network includes a main node with a main wired antenna, and at least one intermediate node with an intermediate wired antenna to be magnetically coupled to a respective device for that intermediate node. An electrical line electrically couples the main node to the at least one intermediate node. At least one electronic device is magnetically coupled to the intermediate wired antenna. A power supply unit is magnetically coupled to the main node via the main wired antenna thereof.

27 Claims, 17 Drawing Sheets

(51) Int. Cl.
*H02J 50/40* (2016.01)
*H02J 7/02* (2016.01)
*H02J 50/70* (2016.01)
*H01L 23/538* (2006.01)
*H01L 23/64* (2006.01)
*H01L 23/66* (2006.01)
*H01L 25/065* (2006.01)
*H01Q 1/22* (2006.01)
*H01Q 7/00* (2006.01)
*H01F 38/14* (2006.01)
*H01Q 1/27* (2006.01)
*H01Q 1/52* (2006.01)
*H02J 50/10* (2016.01)
*A61B 5/00* (2006.01)
*H02J 17/00* (2006.01)

(52) U.S. Cl.
CPC ............ *H01L 23/645* (2013.01); *H01L 23/66* (2013.01); *H01L 25/0655* (2013.01); *H01Q 1/2225* (2013.01); *H01Q 1/273* (2013.01); *H01Q 1/526* (2013.01); *H01Q 7/00* (2013.01); *H02J 7/025* (2013.01); *H02J 50/12* (2016.02); *H02J 50/40* (2016.02); *H02J 50/70* (2016.02); *H04B 5/0031* (2013.01); *H04B 5/0037* (2013.01); *H04B 5/0081* (2013.01); *A61B 5/6804* (2013.01); *A61B 2562/164* (2013.01); *H01L 2223/6677* (2013.01); *H01L 2924/0002* (2013.01); *H01L 2924/3025* (2013.01); *H02J 17/00* (2013.01); *H02J 50/10* (2016.02)

(56) References Cited

U.S. PATENT DOCUMENTS

| | | | |
|---|---|---|---|
| 6,823,171 B1 | 11/2004 | Kaario | |
| 6,884,653 B2 | 4/2005 | Larson | |
| 7,291,907 B2 | 11/2007 | RaghuRam | |
| 7,805,657 B2 | 9/2010 | Kappler et al. | |
| 8,036,168 B2 | 10/2011 | Strutt et al. | |
| 8,085,683 B2 | 12/2011 | Leith et al. | |
| 8,244,187 B2 | 8/2012 | Yoo et al. | |
| 8,301,081 B2 | 10/2012 | Aboba et al. | |
| 8,878,652 B2 | 11/2014 | Tsirline et al. | |
| 9,176,185 B2* | 11/2015 | Canegallo | G01R 31/3025 |
| 9,568,572 B2* | 2/2017 | Vaughan | G01R 33/3692 |
| 2001/0050645 A1* | 12/2001 | Boyle | G06K 19/027 343/702 |
| 2002/0154518 A1* | 10/2002 | Elferich | H02J 7/025 363/15 |
| 2006/0050661 A1 | 3/2006 | Shim et al. | |
| 2006/0249754 A1 | 11/2006 | Forman et al. | |
| 2006/0252284 A1* | 11/2006 | Marmaropoulos | H01R 13/6205 439/37 |
| 2007/0144873 A1 | 6/2007 | Chen | |
| 2007/0222426 A1* | 9/2007 | Waffenschmidt | H01F 38/14 323/355 |
| 2008/0119135 A1* | 5/2008 | Washiro | H04B 5/0012 455/41.1 |
| 2009/0033467 A1 | 2/2009 | Finocchiaro et al. | |
| 2009/0090541 A1 | 4/2009 | Chia | |
| 2009/0117855 A1* | 5/2009 | Rofougaran | H01L 23/66 455/73 |
| 2009/0215391 A1* | 8/2009 | Yoo | H04B 5/00 455/41.1 |
| 2009/0218407 A1 | 9/2009 | Rofougaran et al. | |
| 2010/0164671 A1* | 7/2010 | Pagani | H01L 23/48 336/200 |
| 2010/0210207 A1* | 8/2010 | Goto | G06K 7/0008 455/41.1 |
| 2010/0297954 A1 | 11/2010 | Rofougaran et al. | |
| 2011/0018498 A1* | 1/2011 | Soar | H01F 27/365 320/108 |
| 2011/0019370 A1 | 1/2011 | Koh | |
| 2011/0101788 A1* | 5/2011 | Sun | H01F 38/14 307/104 |
| 2012/0057322 A1* | 3/2012 | Waffenschmidt | H01F 27/365 361/816 |
| 2012/0153740 A1* | 6/2012 | Soar | F41H 1/02 307/104 |
| 2012/0235508 A1* | 9/2012 | Ichikawa | H04B 5/0087 307/104 |
| 2013/0241308 A1* | 9/2013 | Bilbrey | G01R 33/3692 307/104 |
| 2013/0281814 A1* | 10/2013 | Tilt | A61B 5/04085 600/382 |
| 2013/0324041 A1 | 12/2013 | Pagani | |
| 2014/0009266 A1* | 1/2014 | Burnside | G06K 7/10396 340/10.1 |
| 2014/0117927 A1* | 5/2014 | Chateau | H04B 5/0075 320/108 |
| 2017/0093024 A1* | 3/2017 | Pagani | H01L 23/5387 |

FOREIGN PATENT DOCUMENTS

WO WO-2010076187 A2 7/2010
WO WO-2010085671 A1 7/2010

OTHER PUBLICATIONS

Chinese First Office Action and Search Report for CN201380028610.6 dated Feb. 16, 2016 (7 pages).

\* cited by examiner

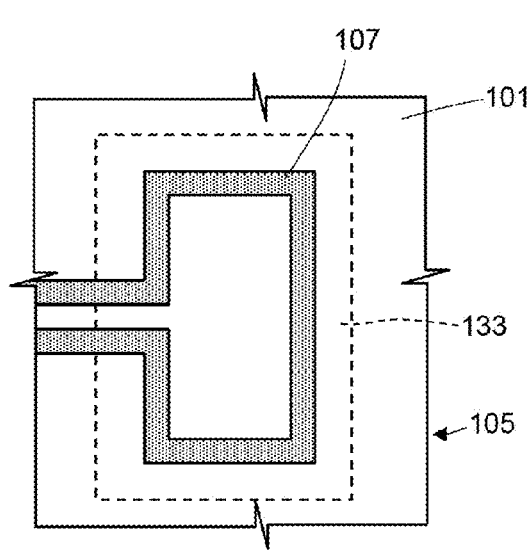
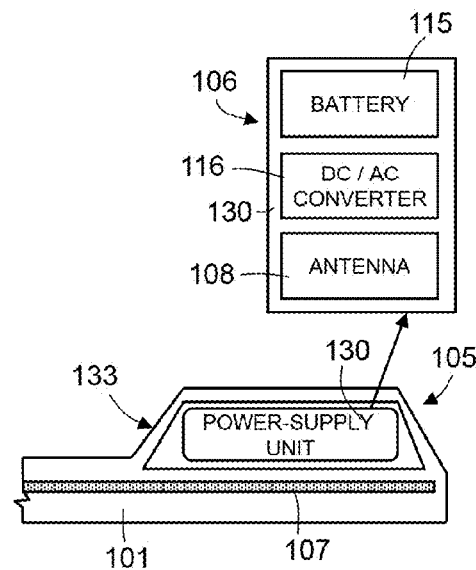
Fig.21a   Fig.21b
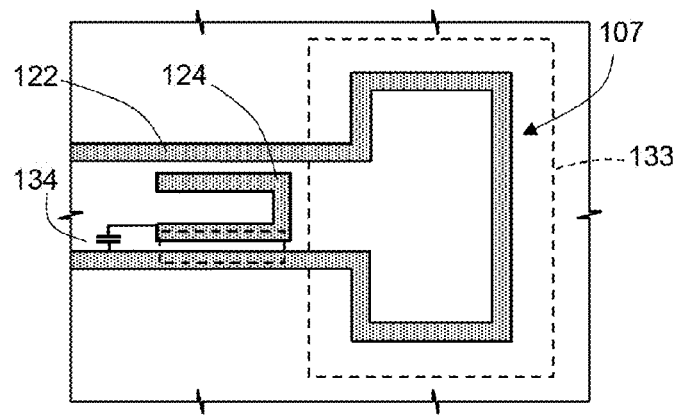
Fig.22a
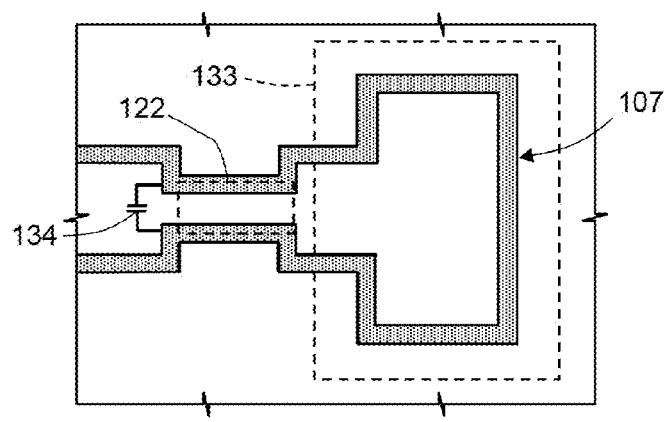
Fig.22b

NETWORK OF ELECTRONIC DEVICES ASSEMBLED ON A FLEXIBLE SUPPORT AND COMMUNICATION METHOD

PRIORITY CLAIM

This application is a continuation of U.S. Ser. No. 13/905,342, filed on May 30, 2013, to be issued as U.S. Pat. No. 9,520,921, and which claims priority to Italian Patent Application No. TO2012A000477 filed May 31, 2012, the contents of which are incorporated in their entirety.

TECHNICAL FIELD

An embodiment relates to a network of electronic devices assembled on a flexible support and to a communication method.

SUMMARY

As is known, the majority of current electronic devices are formed in silicon chips by virtue of the excellent characteristics of this semiconductor material. However, one of the limitations of silicon resides in its lack of flexibility, which prevents use thereof in some applications. For example, silicon is far from suited for application on fabrics or other substrates that, owing to or during their use, may undergo folding. On the other hand, the alternative materials currently under study, such as conductor or semiconductor polymeric materials, have electrical characteristics that are incomparably worse than those of silicon so that they currently do not represent a feasible alternative.

It is thus desirable to provide embodiments that enable implementation of circuits or networks of electronic devices of a flexible type. However, the coupling of electronic devices of a conventional type with flexible supports, for example, a fabric or a plastic support, is problematic.

In fact, currently, the couplings between electronic devices require electrical conductive paths, which, however, entail limitations in the type and degree of flexibility. For example, ribbon couplers of plastic material available on the market may be folded, but the maximum radius of curvature typically must be much greater than the thickness of the coupler, for example, ten times greater. Another limitation resides in the number of bending or folding events that the supports may undergo. For example, some prior couplers allow only a single folding operation, for example during assembly, and cannot modify their spatial arrangement subsequently.

Thus, it is desirable to provide embodiments where the support may undergo events of folding, bending, pulling, twisting, or other types of stress, without undergoing damage, breaking, or creating points and lines of interruption such as to jeopardize the electrical continuity and thus render the entire network unusable.

An embodiment is a network of integrated electronic devices that overcomes the drawbacks of the prior art.

BRIEF DESCRIPTION OF THE DRAWINGS

For a better understanding of the concepts disclosed herein, one or more embodiments are now described, purely by way of non-limiting example, with reference to the attached drawings, wherein:

FIGS. 21a and 21b are, respectively, a top plan view and a cross-sectional view of an embodiment of a node of the network of FIG. 21;

FIGS. 22a, 22b and 23 show variants of the node of FIG. 21 a, in top plan view according to an embodiment;

DETAILED DESCRIPTION

In the embodiments shown in FIGS. 1-17, a flexible substrate 15 carries, embedded inside it, a plurality of devices 1, so as to form a smart panel 20. The devices 1 are electrically separate, but magnetically coupled together.

Figure 1:
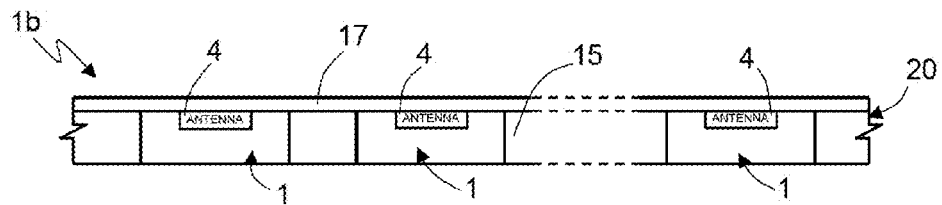
FIGS. 1 and 2 show, in side view and in top plan view, a smart panel or ribbon, according to an embodiment.
Figure 2:
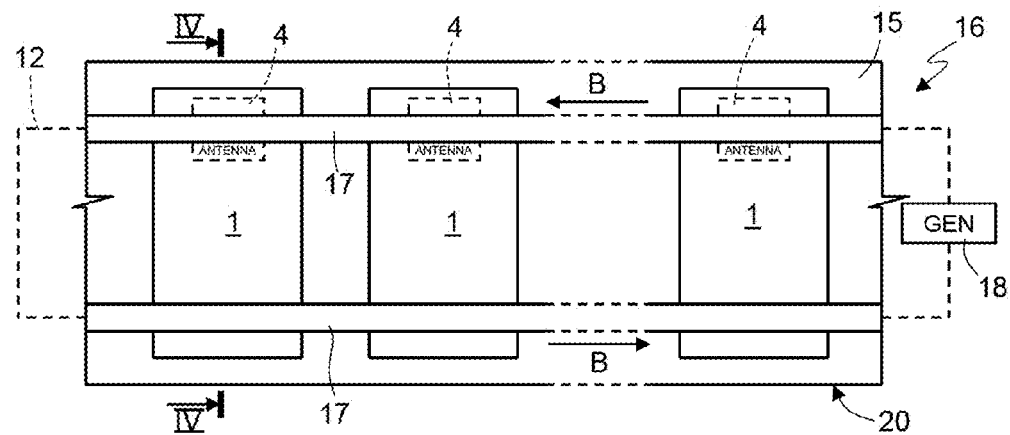

With specific reference to FIGS. 1 and 2, the smart panel 20 is in the form of a ribbon, and the flexible substrate 15 is of flexible material, for example polymeric material such as Kapton or Teflon, which laterally surrounds the devices 1 (as may be noted from FIG. 2), but is level with these at the top and at the bottom, as may be noted from FIG. 1.

The smart panel 20 may have, however, any shape, not necessarily elongated.

The devices 1 have each at least one antenna 4 of a near-field type. Two magnetic strips 17 extend above or inside the flexible substrate 15 in proximity of or contiguous to the antennas 4, and the magnetic strips 17 have a width that is, for example, smaller than the corresponding dimension of the antennas. According to an embodiment, and with reference to the orientation shown in FIG. 2, if the devices 1 have a single antenna 4, this is vertically aligned to one of the two magnetic strips 17 (as shown in FIG. 2); if the devices 2 have two antennas 4, each antenna 4 is arranged vertically aligned with respect to a respective magnetic strip 17 or to coupled magnetic portions, as discussed hereinafter.

The magnetic strips 17 have first ends that may be coupled together (as indicated by the dashed line 12) to form a closed magnetic circuit (with the possibility of interruptions or airgaps), and second ends coupled to a magnetic generator 18, generating, in use, a magnetic field B. In this way, as shown in FIG. 2, the magnetic field B is substantially confined within the two magnetic strips 17 and is oriented in each of them in an opposite direction. In practice, the magnetic strips 17 form a magnetic circuit, which, thanks to the coupling with the antennas 4, couples the devices 1 in a network 14.

The magnetic circuit enables efficient transmission of signals and power between the devices 1 in absence of physical or electrical contact. Furthermore, any possible failure of the magnetic strips 17, for example as a result of repeated folding of the flexible substrate 15, does not interrupt the circuit. Moreover, because of the magnetic coupling between the antennas 4 and the strips 17, no electrical-contact pads or regions are necessary on the flexible substrate 15, which could reduce the flexibility thereof and may undergo damage. In addition, it is not required for the strips 17 to be continuous, but gaps, i.e., absence of magnetic material in one or more short stretches, may exist or arise without this implying interruption and thus malfunctioning of the network 14. In this way, if mechanical stresses, folds with a small radius of curvature, or repeated folding or stresses of any other kind (including aging) were to lead to discontinuities of the magnetic strips 17, this would not jeopardize communication between the devices 1 or between the devices and their supply.

The network 16 of FIGS. 1 and 2 may be obtained in the following way: initially the devices 1 are glued on a supporting plate, for example, provided with an adhesive surface; then the plastic material is applied in a liquid or molten condition, at a temperature such as not to damage the devices 1, for example by spinning; next, polymerization and hardening of the plastic material is carried out; and finally the excess plastic material parts are removed from the top surface, for example by etching and planarization until the devices 1 are exposed, if so desired. Finally, if necessary, the obtained structure is cut into the desired shapes or divided into various parts, for example various ribbons.

The magnetic strips 17 may be obtained, for example, by inkjet printing, using an ink used in the semiconductor industry containing magnetic particles. As an alternative, the technique of aerosol printing of magnetic material may be used, or the magnetic strips 17 may be pre-molded and applied. For example, the magnetic strips 17 may be of soft magnetic material, such as CoZrTa, FeHfH(O) and the like, chosen also on the basis of the frequencies used for communications between the devices 1. If high frequencies are used, of the order of some gigahertz, then the material may be subject to thermal annealing steps in the presence of a magnetic field (magnetic annealing) to optimize the characteristics of the magnetic material.

Alternatively, as discussed hereinafter with reference to FIG. 4a, the polymeric material parts of the flexible substrate 15 surrounding the devices 1 also at the top are not removed. In this case, it is also possible to apply a polymeric material layer on the rear side of the panel 20, after it has been flipped over. In this case, the devices 1 are completely embedded in the flexible substrate 15. It is also possible to apply the further polymeric material layer after forming of the magnetic strips 17, thereby embedding the strips within the panel 20.

Figure 3:
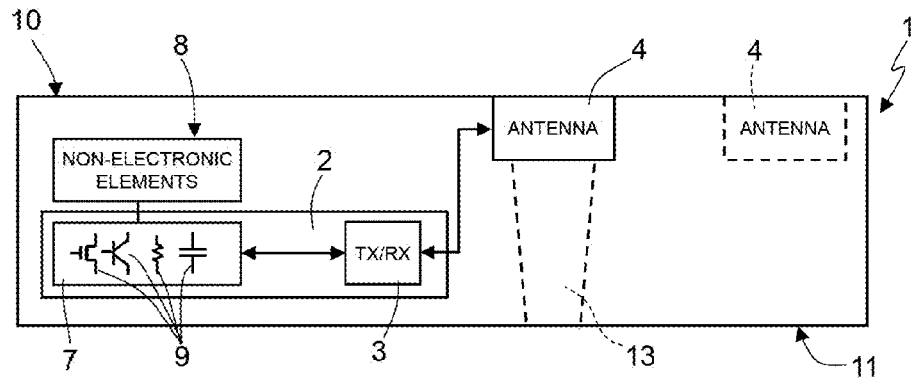
FIG. 3 is a block diagram of a device belonging to the present network according to an embodiment.

FIG. 3 shows the basic structure of a device 1 forming part of the network 14 of FIGS. 1 and 2 according to an embodiment. In its basic structure, each device 1 includes an electronic part 2 and the antenna 4. In addition, one or more non-electronic elements 8 may be provided, coupled to the electronic part 2. The device 1 may also include more than one antenna, for example, two antennas 4, as discussed hereinafter.

In turn, the electronic part 2 includes an integrated circuit 7 and a transceiver circuit 3.

For example, the integrated circuit 7 (schematically represented in the figure by electronic components 9) may operate, possibly together with the non-electronic components 8, as a sensor, actuator, interface, or electrode; in addition, the integrated circuit 7 may be a memory, a control unit, a microprocessor, a microcontroller, a power-supply unit, a converter, an adapter, a digital circuit, an analog circuit, an RF circuit, etc.

The non-electronic element or elements 8, of an electrical/mechanical/chemical type, may be, for example, microelectromechanical systems (MEMS, NEMS, for example constituting sensors or actuators), or electrodes, wells, cells, vials for liquids, microchannels, etc.

The transceiver circuit 3 may be physically separate from the integrated circuit 7 or together therewith.

The transceiver circuit 3 has the function of coupling the integrated circuit 7 to the antenna 4 for transmitting or receiving signals or power and typically includes a transponder or a transceiver and AC/DC or DC/AC converter circuits.

Each antenna 4 is formed in the proximity of a main surface 10 of the device 1 or faces said surface, and is generally provided as loop antenna (with one turn or multiple turns), even though it is possible to use jointly other types of antennas, such as, for example, Hertzian dipoles, or interfaces of a capacitive type. In particular, the antenna may be obtained following the teachings of patent application No. WO 2010/076187, which is incorporated by reference.

The device 1 may further include a magnetic via 13, extending inside the device, underneath the antenna 4 (with respect to the main surface 10) or within the antenna 4 (as described, for example, in aforesaid patent application WO 2010/076187) as far as a second main surface 11 opposite to the first main surface 10; the magnetic via 13 is electrically uncoupled from the antenna 4. The magnetic via 13 is, for example, shaped like a truncated pyramid or a truncated cone set upside down.

As has been mentioned, the device 1 may be formed by a semiconductor chip or by a complex system. Typically, if the integrated device 1 is formed by a chip (as shown, for example, in FIG. 4*a*), this includes a semiconductor substrate 21 and a dielectric layer 22. The semiconductor substrate 21, for example of silicon, houses the electronic part 2 and possibly the non-electronic elements 8 (at least partially, since, in some applications, these may project from the device 1). The dielectric layer 22 houses antenna or antennas 4 and the possible internal couplings of conductive material, for example metal, which form various metallization levels coupled by vias, in a per se known manner, not shown.

Instead, if the integrated device 1 is a more complex system, it may be formed by a package housing packaged systems and devices, for example SoCs (Systems-on-Chip), SiPs (Systems-in-Package), in turn integrating the electronic part 2 or the non-electronic elements 8, and the antenna or antennas 4. For example, the device 1 may be packaged using a technique similar to the wafer-level chip-scale packaging, applying a resin for moulding on a main surface and on the sides of the wafer, turning over the wafer, and providing the rest of the system on the free face.

Figure 4A:
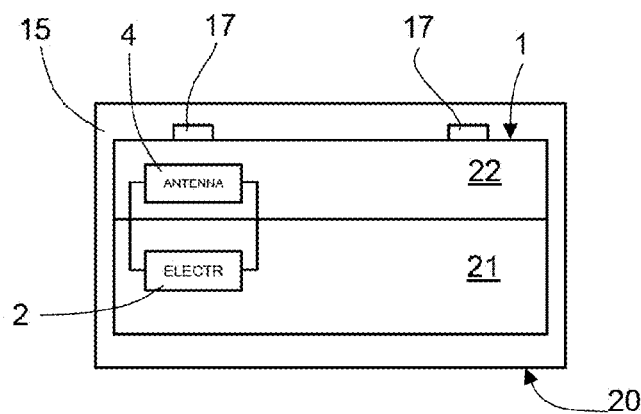
FIGS. 4a, 4b and 4c show cross-sections, taken along section plane IV-IV of FIG. 2, of two different embodiments of the device of FIG. 1.

For example, in the embodiment of FIG. 4*a*, the device 1 is formed by a chip. Moreover, here, the flexible substrate 15 completely surrounds the device 1 and the magnetic strips 17. Alternatively, as indicated, the flexible substrate 15 may be flush or level with the top or bottom surface of the chip, and the magnetic strips 17 may extend over the flexible substrate 15; in addition, the chip 1 may have two antennas 4.

Figure 4B:
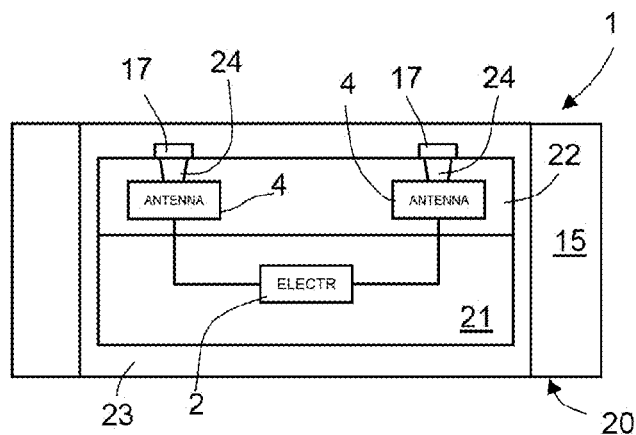

FIG. 4*b* shows a device 1 formed by a chip, here coated, on its entire outer surface, by a package 23 of moulded resin. In this case, at least one magnetic via 24 is formed through the package 23, vertically aligned to the antenna 4 and to one of the two magnetic strips 17. In the example shown, the device 1 has two antennas 4; consequently, two magnetic vias 24 are present, in direct contact with the respective magnetic strips 17. Here, the flexible substrate 15 surrounds the device 1 only laterally, but could surround it also at the top or at the bottom.

In this way, the device 1 is sturdier, since it is protected on the outside by the package 23.

In the device 1 of FIG. 4*b*, the antennas 4, the magnetic vias 24, and the magnetic strips 17 are all arranged on a same side (top side) of the device 1.

However, they may be arranged both in the top portion and in the bottom portion of the device 1. For example, in a variant not shown, both the antennas 4, just one magnetic via 24, and just one magnetic strip 17 may be arranged in the top part of the device 1, and the other magnetic via 24 and the other magnetic strip 17 may be arranged in the bottom part. In this case, a magnetic path (not shown) that laterally surrounds the device 1 may couple the magnetic via arranged at the bottom to the corresponding antenna arranged at the top, or alternatively a magnetic via 13 similar to that of FIG. 3 may be formed.

Figure 4C:
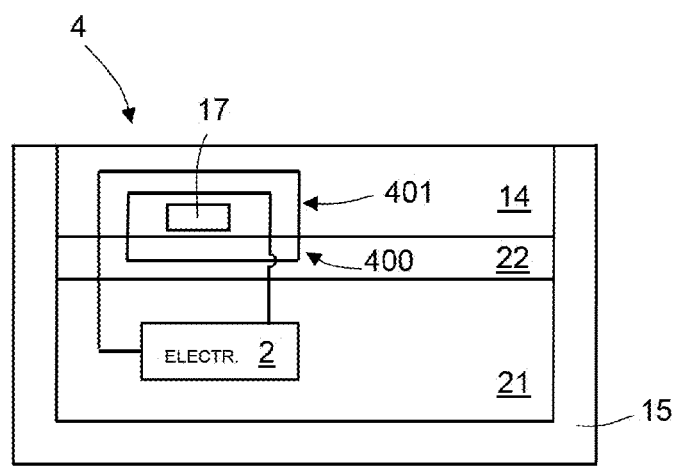

In an embodiment shown in FIG. 4*c*, the antenna 4 is no longer provided substantially parallel to the surfaces 10 and 11 of the device 1, but extends substantially parallel to a vertical plane. For example, the antenna 4 may be formed in part (first portion 400) in the dielectric layer 22 of the device 1, and in part (second portion 401) in a top layer 14, formed by the flexible substrate 15 (similarly to FIG. 4*a*) or by a separate layer, such as a flexible printed-circuit board. In this way, the antenna 4 may surround the magnetic strip 17. The second portion 401 may be obtained with known techniques, such as, for example, via wire bonding or paths of conductive material coupled to contact pads (not shown) of the device 1. In a variant, the second portion 401 may be surrounded by or included in a package 23 similar to FIG. 4*b*. In addition, even though FIG. 4*c* shows the antenna 4 formed by two turns, the number of turns may be different (one or more than two).

Figure 5:
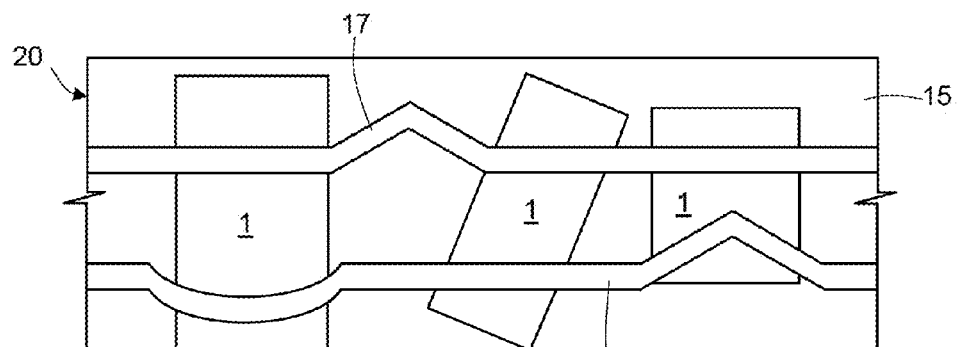
FIG. 5 shows a different embodiment of the present network, in top plan view.

FIG. 5 shows an embodiment where the magnetic strips 17 are not shaped as straight lines, but are formed by segments of any shape, or are even curved. Such an embodiment may prove advantageous when the flexible substrate 15 undergoes frequent folding and bending since it bestows a greater flexibility on the magnetic strips 17, above all in the direction transverse to the length of the smart panel 20. The flexibility of the magnetic strips 17 may also be increased if each of them is formed by the superposition of a plurality of layers, in which case their flexibility is increased in the direction of the thickness of the smart panel 20.

Furthermore, in FIG. 5, also the devices 1 are arranged in a non-aligned way with respect to the longitudinal direction of the smart panel 20.

Figure 6:
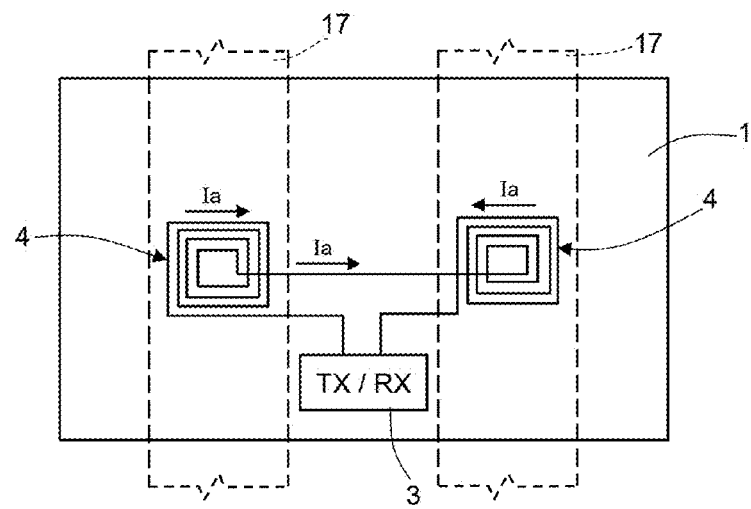
FIGS. 6 and 7 show cross-sections of possible embodiments of a detail of the device of FIG. 3.
Figure 7:
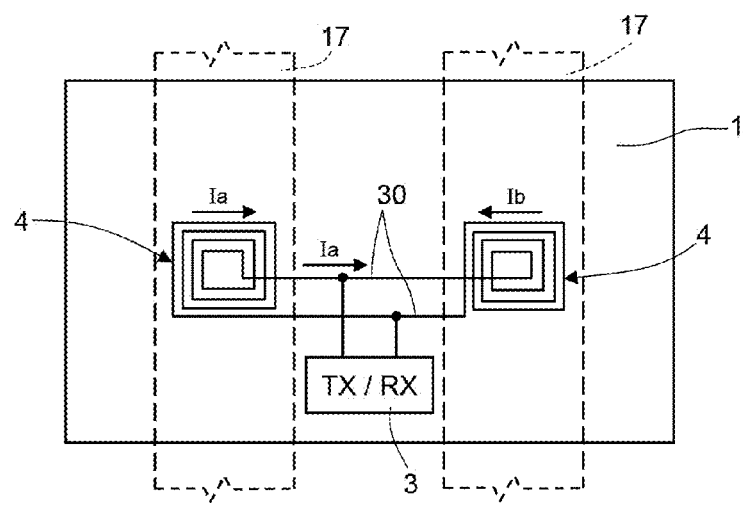

FIGS. 6 and 7 show two alternatives of coupling between two antennas 4 and the transceiver 3 of a same device 1. In FIG. 6, the antennas 4 are arranged in series with respect to one another and to the transceiver 3. Thus, as a result of the magnetic field B concentrated in the magnetic strips 17, a current Ia is generated within the antennas 4, having the same amplitude in both antennas, but traversing the turns of the two antennas 4 in opposite directions. In practice, in one of the two antennas 4 there is a conversion of energy from magnetic into electrical and in the other antenna 4 there is a conversion of energy from electrical to magnetic.

By introducing a modulation of the magnetic field, it is possible to transmit and receive electrical signals. In fact, the current Ia generated in a first of the two antennas 4 flows also in the transceiver 3, which thus, in addition to extracting power, extracts the modulated electrical signals at input and transmits them to the integrated circuit 7 (FIG. 3). In addition, the transceiver 3 receives electrical output signals from the integrated circuit 7, supplies them to the other antenna 4, and this transmits the signals to the magnetic strip 17 coupled thereto. The transceiver 3, in particular, may contain an AC/DC and DC/AC converter. Transmission and reception may moreover take place in both antennas.

For example, the modulation could be of an ASK (Amplitude Shift Keying) type and regard 10% of the amplitude of the magnetic field B, while the remaining 90% is dedicated to power supply. The frequencies that may be used may be, for example, in approximately the 10 MHz-10 GHz range.

FIG. 7 shows a solution with parallel coupling. Here, the two antennas 4 are coupled together via two lines 30, and the transceiver 3 is coupled with a first terminal to one of the two lines and with a second terminal to the other line 30. In this case, one of the two antennas 4 is traversed by a first current Ia, and the other antenna 4 is traversed by a second current Ib.

In a variant not shown, each of the two antennas 4 is coupled to a respective pair of terminals of the transceiver 3 (which is a quadrupole). In this way, there is a cascaded coupling between the first antenna, the transceiver, and the second antenna, and thus the two antennas 4 of the device 1 are not directly coupled together.

Also further variants are possible. In particular, if the device 1 integrates two integrated circuits 7, these may be coupled both in series, both in parallel, or one in series and the other in parallel, in a way not shown.

Figure 8:
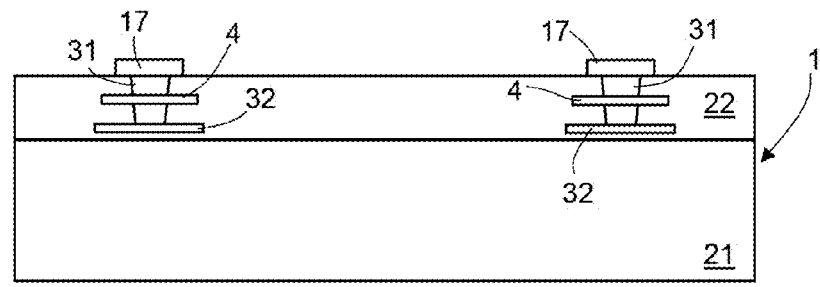
FIGS. 8 and 9 are cross-sections of a detail of the device of FIG. 3 according to an embodiment.

In FIG. 8, two magnetic vias 31 extend through the dielectric layer 22 and through respective antennas 4, vertically aligned to a respective magnetic strip 17. Two magnetic regions 32 extend underneath the antennas 4, each coupled to a respective magnetic via 31.

The magnetic regions 32 enable closing of the lines of force of the magnetic field and increase of the coupling between the antennas 4 and the corresponding magnetic strips 17.

As an alternative to FIG. 8, it may be possible to have a single magnetic via 31 and a single magnetic region 32, in particular if just one antenna 4 is present.

Figure 9:
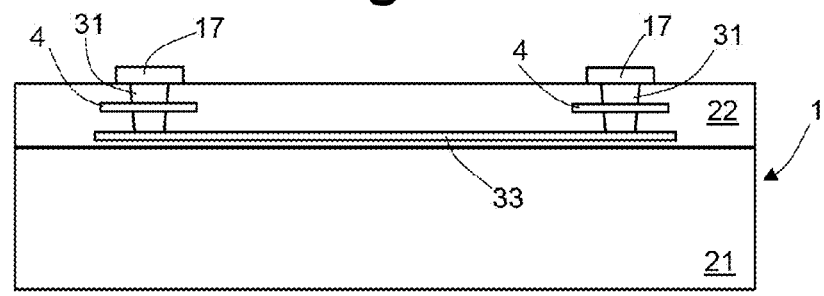

FIG. 9 shows an embodiment with a single magnetic region 33 extending between the two magnetic vias 31. In an alternative embodiment, the magnetic region 33 extends between the two antennas 4, underneath them, even in absence of the magnetic vias 31. In yet another alternative (not shown), it may be possible to have just one antenna 4, traversed by a first magnetic via 31 coupled to a second magnetic via 31 without an antenna. The embodiment of FIG. 9 and the alternatives described enable closure of the magnetic field and may be used for the last device 1 so as to implement the coupling 12 of FIG. 2, or also in an intermediate way so as to have a plurality of closure points of the magnetic field in a distributed way.

Figure 10:
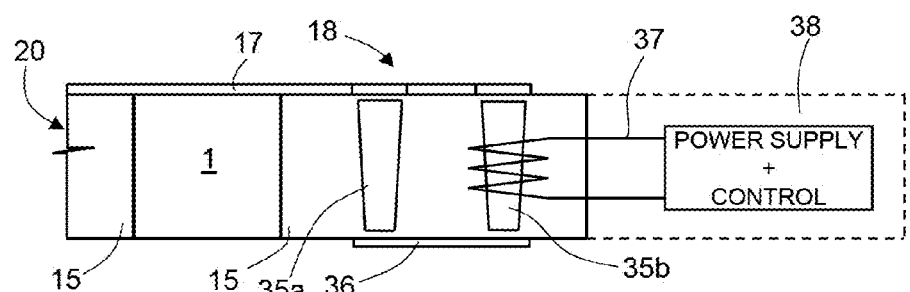
FIG. 10 shows a cross-section of a terminal portion of the present network according to an embodiment.
Figure 11:
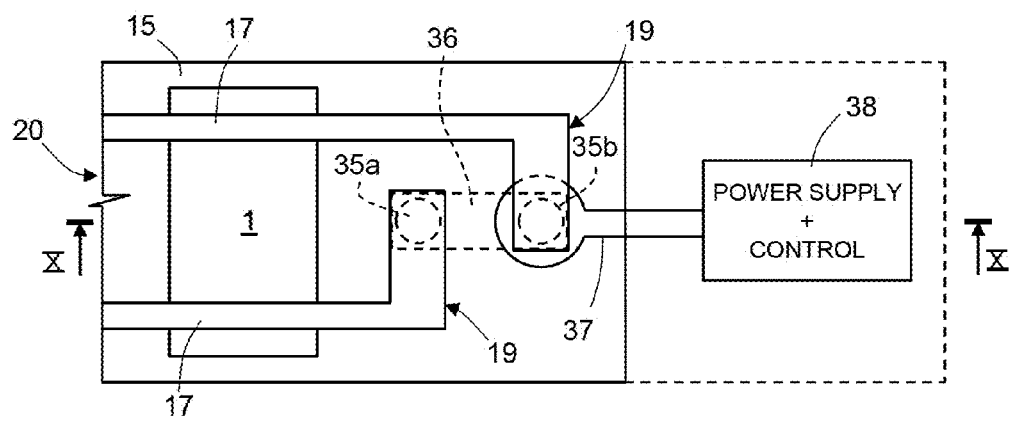
FIG. 11 is a top plan view of the portion of FIG. 10 according to an embodiment.

FIGS. 10 and 11 show a possible implementation of the coupling of the magnetic strips 17 to the magnetic generator 18. In detail, two final magnetic vias 35a, 35b extend underneath the second ends 19 of the magnetic strips, through the entire thickness of the flexible substrate 15, and have, for example, the shape of a truncated cone, and end in proximity of a closure or closing region 36.

The closing region 36 is of magnetic material and extends on the rear side of the panel 20, between the final magnetic vias 35a, 35b so as to close the magnetic circuit. A conductor 37, for example a metal wire, is wound around one of the final magnetic vias 35a, 35b, here the final magnetic via 35b, and is coupled to a power-supply unit 38. The power-supply unit 38 includes a radio-frequency AC current source and control electronics, of a known type, and may be external (as represented with a solid line) or embedded in the flexible substrate (as represented with a dashed line). In practice, the conductor 37 forms an electric winding that transforms the AC current supplied by the power-supply unit 38 into the magnetic field B. The radio-frequency AC current source generates at least one signal (for example, a sinusoid, a square wave, a triangular wave) at least one frequency. In one variant, a signal at a first frequency F0 may supply a plurality of devices 1, and a set of signals or carriers at different frequencies F1-Fn may be used by various devices 1 for communicating with each other. The power-supply unit 38 may possibly also include transceiver circuits for enabling an external system to communicate with the smart panel 20, or for enabling passage of information from one carrier at the frequency Fi to a carrier at the frequency Fj.

Figure 12:
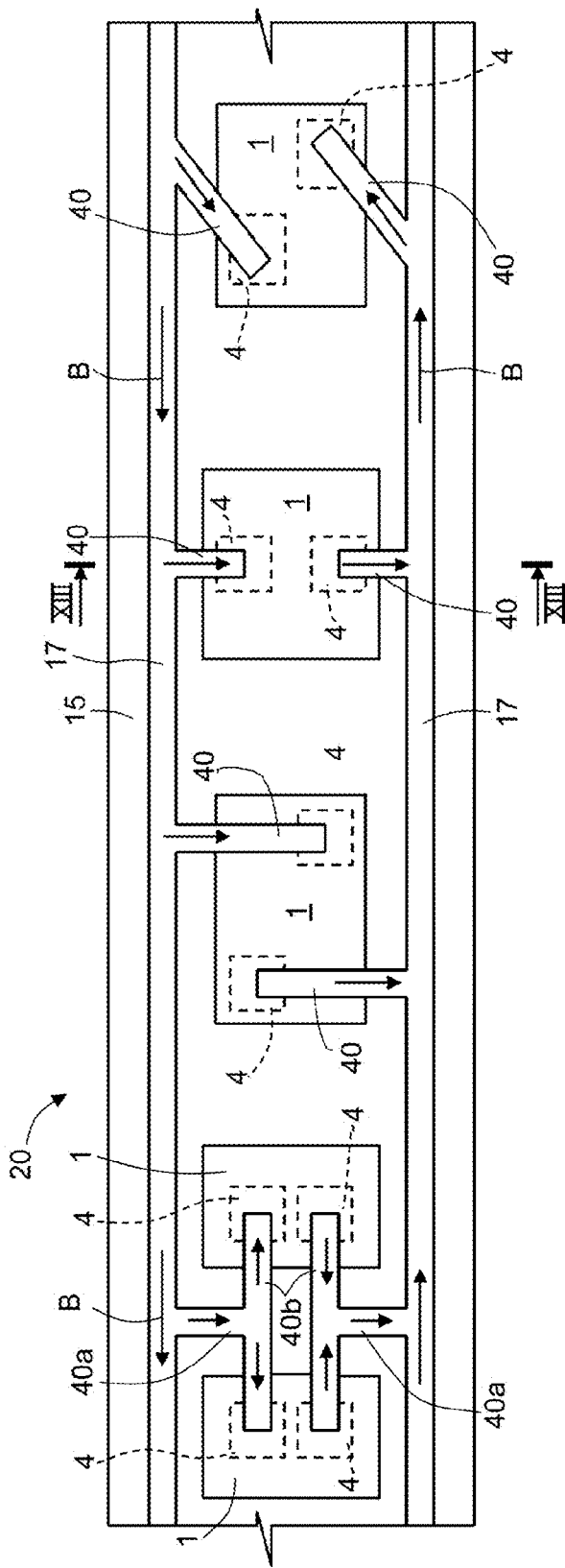
FIG. 12 shows different embodiments of the present network, in top plan view.

FIG. 12 shows a different conformation of the strips 17, which, instead of extending over the devices 1, extend alongside the latter and are provided with projections 40 ending on top of the devices 1. In practice, the projections 40, four different pairs shown in the figure, extend transverse to the magnetic strips 17. In the three pairs of projections further to the right, the projections are each formed by a single segment that ends above a respective antenna 4. In the pair further to the left, the projections 40 are formed by a first segment 40a extending from and transverse to a respective magnetic strip 17 and by a second segment 40b extending from and transverse to the first segment 40a and ending at the antennas 4 of two adjacent devices 1.

In FIG. 12, the arrows indicate the direction of the magnetic field B in the projections 40.

Figure 13:
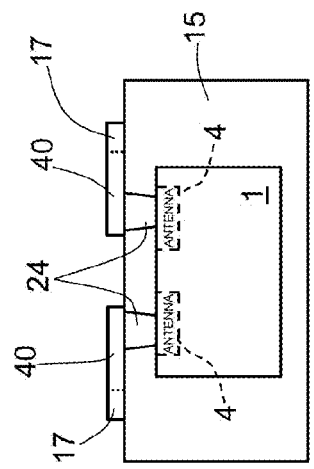
FIG. 13 is a cross-section of an embodiment of FIG. 12.

The projections 40 are formed together with the magnetic strips 17, of the same material and with the same thickness, as may be seen in the cross-section of FIG. 13, where the device 1 is completely embedded in the flexible substrate 15. Magnetic vias 24, similar to the homologous ones of FIG. 4b, may be provided in the flexible substrate 15, between the projections 40 and the antennas 4.

Figure 14:
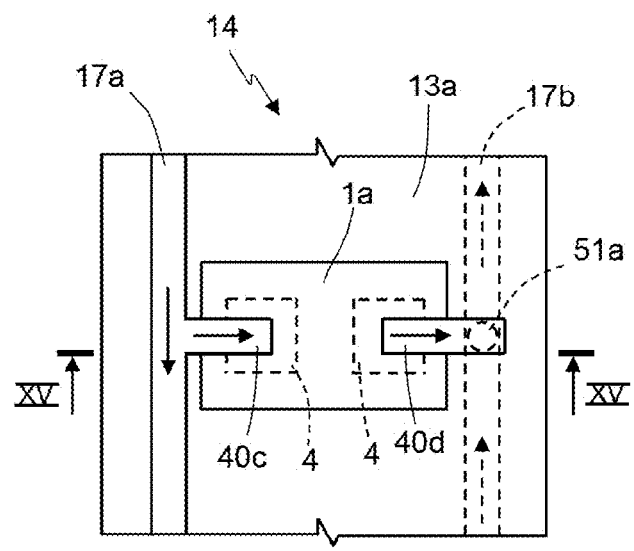
FIGS. 14 and 15 show a different embodiment of the present network, respectively in top plan view and in perspective sectional view taken along the plane XV-XV of FIG. 14.
Figure 15:
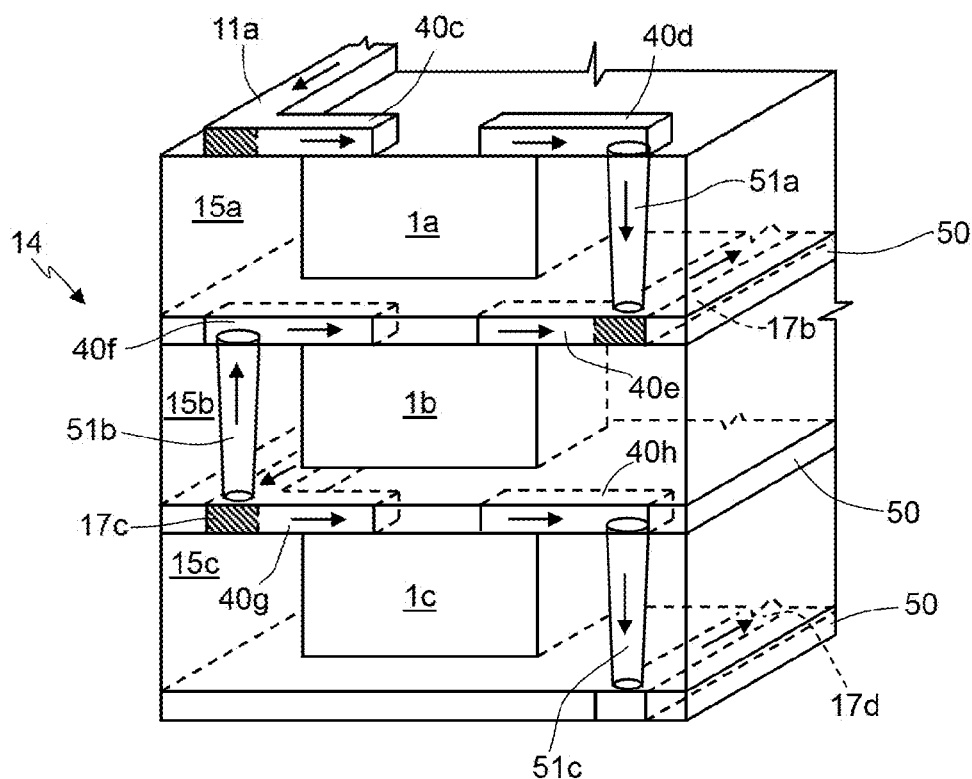

FIGS. 14-15 show a network 14 where the devices 1 are arranged on different levels and are coupled to magnetic strips 17, which are also arranged on more levels. In practice, each level is formed by a flexible support 15 housing a plurality of devices 1 and magnetic strips 17 forming one or more magnetic circuits magnetically coupled to the devices 1.

The shown example has three levels, the elements whereof are identified by the letters a, b and c. The devices in the top level are designated by 1a, the devices in the intermediate level are designated by 1b, and the devices in the bottom level are designated by 1c, these devices being surrounded, respectively, by a top flexible support 15a, an intermediate flexible support 15b, and a bottom flexible support 15c.

Here, the devices 1a, 1b and 1c are coupled to magnetic strips 17a-17d, which extend on four different surfaces so as to reduce the number of magnetic strips 17. In the example shown, a first magnetic strip 17a (where the magnetic field has a first direction, see FIG. 15) extends over the top flexible support 15a; a second magnetic strip 17b (where the magnetic field has a second, opposite, direction) extends between the top flexible support 15a and the intermediate flexible support 15b, surrounded by insulating or dielectric material 50 (which may be of the same type as the type of material used for the flexible support); a third magnetic strip 17c (where the magnetic field has the first direction) extends between the intermediate flexible support 15b and the bottom flexible support 15c, surrounded by the dielectric material 50; and the fourth magnetic strip 17d (where the magnetic field has the second direction) extends underneath the bottom flexible support 15c, surrounded by the dielectric material 50.

The first magnetic strip 17a is coupled to the devices 1a of the top level via first projections 40c coplanar to the first magnetic strip 17a. The second magnetic strip 17b is coupled to the devices 1a of the top level via second projections 40d coplanar to the first magnetic strip 17a and magnetic coupling vias 51a traversing the first flexible substrate 15a. The second magnetic strip 17b is moreover coupled to the devices 1b of the intermediate level through third projections 40e. The third magnetic strip 17c is coupled to the devices 1b of the intermediate level through fourth projections 40f and magnetic coupling vias 51b traversing the second flexible substrate 15b. The third magnetic strip 17c is moreover coupled to the devices 1c of the bottom level through fifth projections 40g coplanar to the third magnetic strip 17c. The fourth magnetic strip 17d is coupled to the devices 1c of the bottom level through sixth projections 40h and magnetic coupling vias 51c traversing the third flexible substrate 15c.

Of course, the projections 40a-40h could be provided in any of the ways shown in FIG. 12; for example, each projection 40a-40h may be formed by a plurality of segments, be aligned or staggered, or inclined in different ways.

By virtue of the plurality of levels, it is possible to have a plurality of magnetic generators 18.

Figure 16:
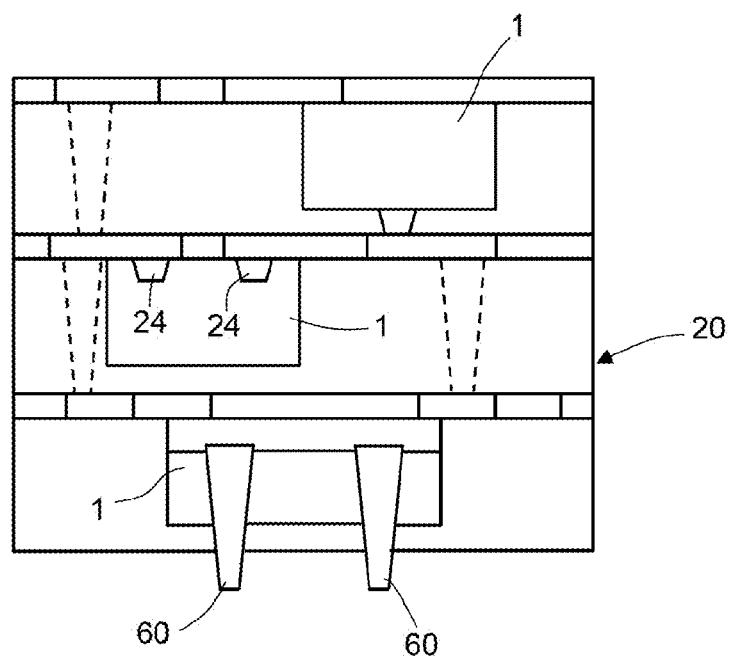
FIG. 16 shows a different embodiment of the present network, in cross-sectional view.

FIG. 16 shows an embodiment with more levels, or a stacked embodiment, and the device 1 arranged on the bottom level carries needles 60 having microchannels and projecting at the bottom from the panel 20, for enabling injection of liquids in wells (not shown) housed in the device 1. The device 1 arranged at the intermediate level is a SiP (System in Package) having magnetic vias 24 between the magnetic strips 17 and the antennas 4 (not shown), and the top device 1 may be an ASIC with a possible MEMS device, for example operating as a transducer. Alternatively, the bottom device 1 may carry electrodes (not shown) facing the bottom surface of the panel 20, for application of stimuli to a surface to which the panel is applied (for example, the skin) for carrying out stimulation in order to measure biological parameters and the like.

Figure 17:
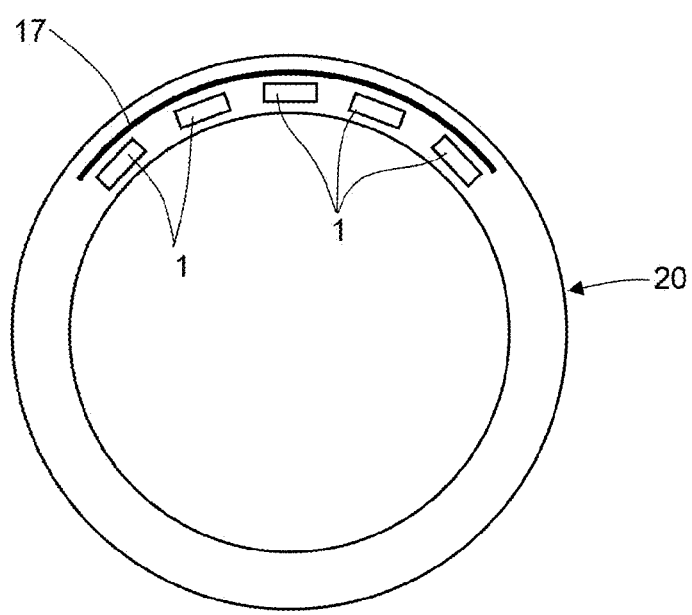
FIG. 17 shows a different embodiment of the present network in top plan view.

FIG. 17 shows an embodiment of the present network 14 wherein the panel 20 is configured as a ring so that it may be fitted on the human body or on an animal, for example as bracelet, collar, thigh strap, waist belt and the like. For example, the panel may form a flexible bracelet, for instance, a watch bracelet.

The panel 20 may be continuous or provided with an openable fastener and houses a plurality of devices 1 and one or more magnetic strips 17 so as to form a flexible and foldable apparatus such as a cell phone, a tablet, a television set, a computer, a medical apparatus, or the like, associated, if so desired, with a traditional wrist watch.

In the embodiments shown in FIGS. 18-39, a smart network is formed on a same fabric, on a same garment, on different portions not coupled together of a same garment, or on a plurality of garments. Here, the network is divided into a plurality of systems, which, thanks to the contained dimensions of each system, are inserted in smart buttons. Hereinafter, the divided systems are referred to as "devices" by analogy with the embodiment of FIGS. 1-17.

Here, each device inserted in a smart button has an embedded antenna that enables coupling with the other devices of the network in wireless mode using passive wired conductive lines, provided with wired antennas at nodes of the network. The smart buttons are arranged at the nodes and receive energy via an electromagnetic concentrator/expander.

Figure 18:
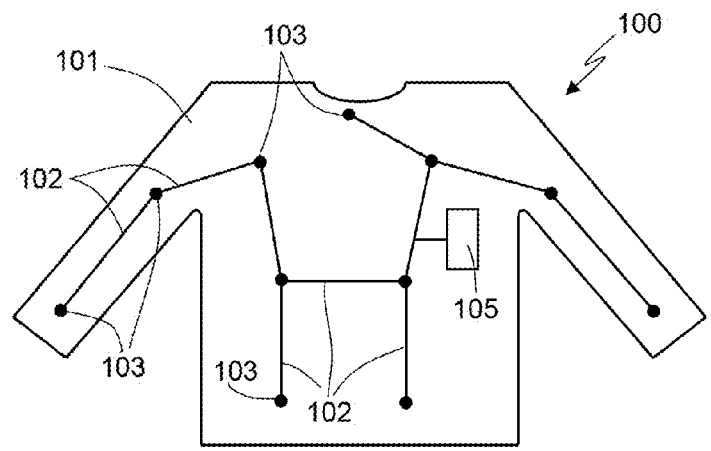
FIG. 18 shows another embodiment of the present network to be applied to a garment.
Figure 19:
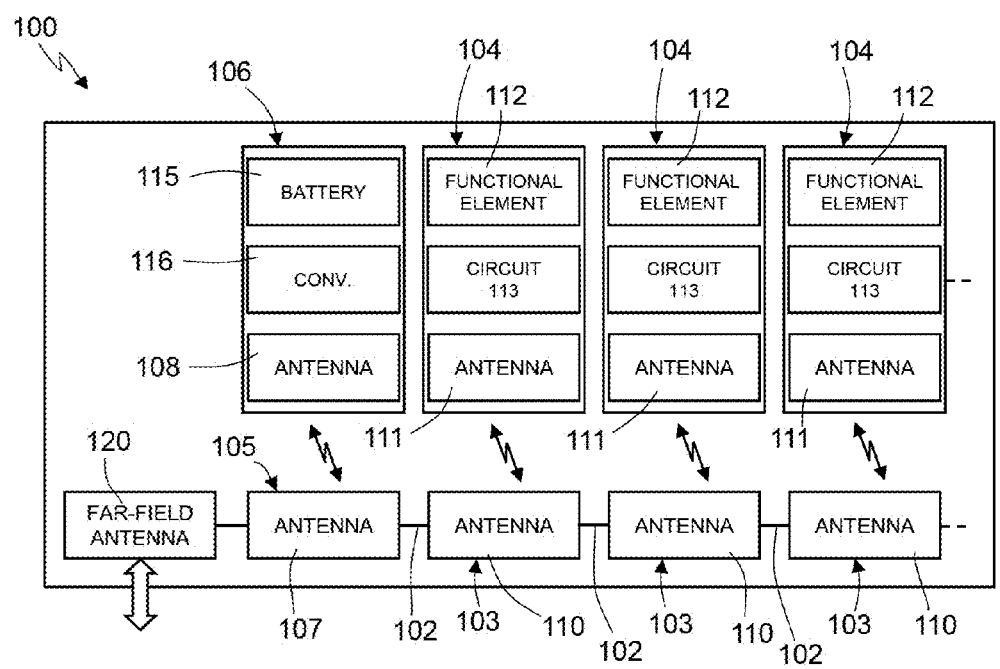
FIG. 19 is a block diagram of the network of FIG. 18 according to an embodiment.

In detail, FIGS. 18 and 19 show the structure of a network 100, formed on a garment 101. The network 100 includes an electrical line 102 extending on the fabric of the garment 101 and electrically coupling together a plurality of intermediate nodes 103. In turn, each intermediate node 103 is magnetically coupled to a respective device 104 (FIG. 19) housed in a smart button. The network 100 further includes a main node 105 coupled to a power-supply unit 106, for supply of the network. As shown in particular in FIG. 19, each intermediate node 103 is basically formed by a wired antenna 110. Each device 104 may be basically formed as the device 1 of FIGS. 1-17 and may include at least one semiconductor chip or form a complex system, for example a SiP. Basically, each device 104 includes an embedded antenna 111, coupled to a respective wired antenna 110, one or more functional elements 112, and one or more electronic circuits 113. Here, in general, and similarly to the non-electronic elements 8 of FIG. 3, the functional elements 112 include one or more non-electronic elements, of an electrical/mechanical/chemical type, such as microelectromechanical systems (MEMS, for example forming sensors or actuators or more in general transducers), or interfaces, electrodes, wells, cells containing liquids, etc., and the electronic circuits 113 (equivalent to the electronic part 2 of FIG. 3) may include memory elements, control units, converters, adapters, digital circuits, analog circuits, or RF circuits, in addition to a transceiver circuit similar to the circuit 3 of FIG. 3.

Also the power-supply unit 106 includes an embedded antenna 108, coupled to a respective wired antenna 107 of the main node 105, a battery or a set of batteries 115, and a DC/AC converter 116, coupled between the battery 115 and the embedded antenna 108. The power-supply unit 106 may moreover include a memory for storing the data transmitted by the devices 104 through the corresponding intermediate nodes 103 and may be coupled to a cell phone (not shown) for exchanging data with other external systems, even remote ones.

Furthermore, in FIG. 19 a far-field antenna 120 is provided for enabling coupling with the external environment, for example with a further garment or a generic electronic system, and is coupled with the network 100 through the electrical line 102.

The electrical line 102 may be formed by a single conductive wire that may possibly be welded at the ends and forms both the loops of the antennas 107, 110 (as discussed hereinafter) and the forward and return lines or partly forward and partly return lines. Alternatively, the electrical line 102 may be formed by a plurality of conductive wires, arranged on top of or embedded in the material of the garment 101. The electrical line 102 may be made of one or more conductive materials, for example copper, aluminium, tungsten, gold, silver, nickel, platinum, or their alloys. The electrical line 102 may be considered as a transmission line that may be of a known type, for example of a twin-lead type or of a GSG (Ground Signal Ground) or GSSG (Ground Signal Signal Ground) type or the like.

Figure 20A:
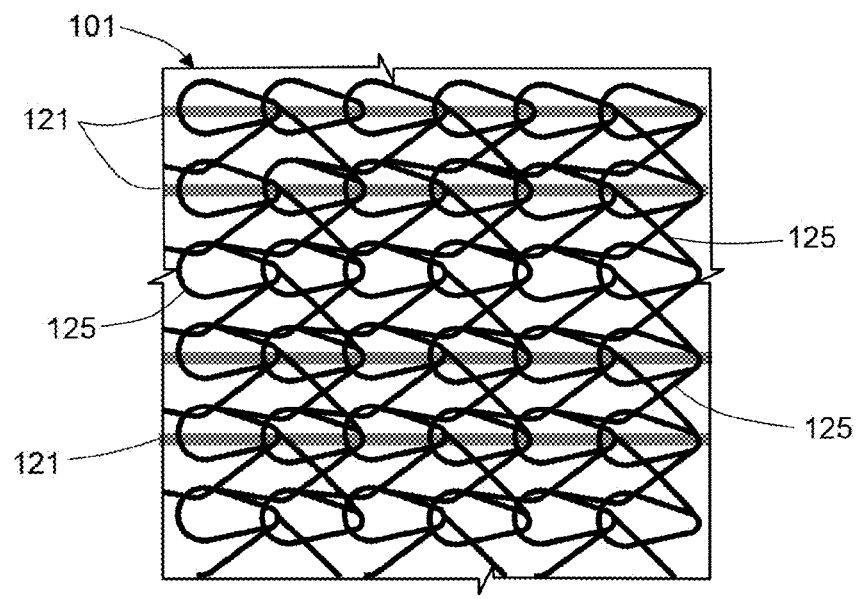
FIGS. 20a and 20b show two examples of conductive wires that may be used in the network of FIG. 18 according to an embodiment.

For example, FIG. 20a shows an embodiment where the garment 101 is formed by a knitted fabric. In this embodiment, the knitted fabric is formed by a plurality of yarns 125, and conductive wires 121 extend therethrough and are made, for example, of copper or aluminium. Alternatively, the conductive wires 121 may be formed by optical fibres, or even the optical fibres, generally of flexible material, may be knitted selectively together with the yarns 120 and form part of the fabric material.

Figure 20B:
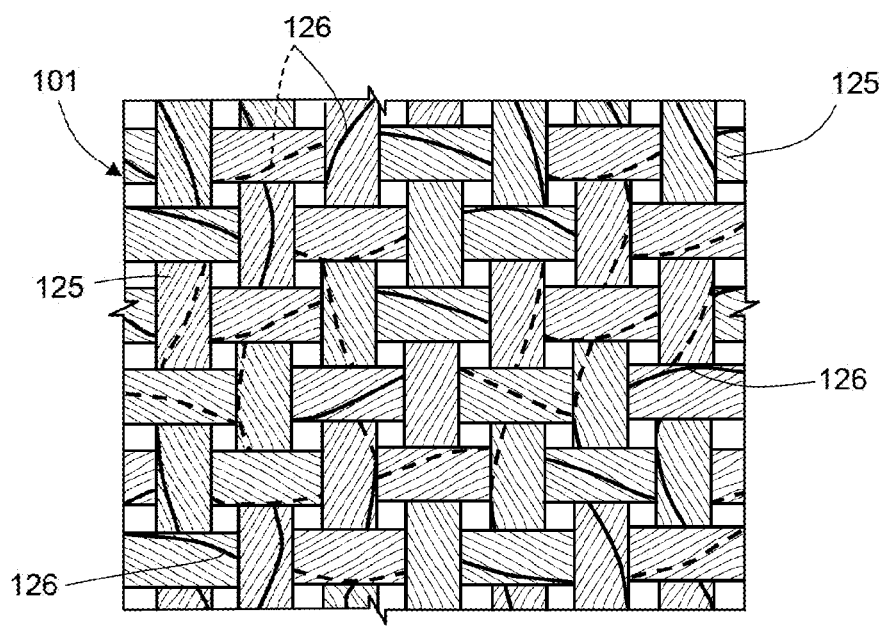

FIG. 20b shows a different embodiment, where the fabric is woven and is formed by standard weft and warp yarns 125, and electrical wires 126, for example of copper or aluminium, are embedded directly within at least some of the yarns 125, for example twisted simultaneously therewith.

In both embodiments, the electrical wires 121 and 126 are generally insulated; for example, they are have a sheath or a dielectric coating.

The network 100 is thus of a modular type, and the devices 104 (some embodiments whereof are described hereinafter) are interchangeable so as to enable devices 104 having different functional elements 112 to be positioned each time according to the application. This enables systems to be obtained that globally have characteristics even markedly different from each other on the basis of the type of smart buttons used.

The devices 104, the power-supply unit 106, and the garment 101 are manufactured separately and are galvanically insulated from one another, thus rendering the system very reliable, flexible, repairable, configurable, and suited for being worn. The garment 101 may also be washed in a conventional way, for example, after prior removal of the smart buttons to prevent damage to the smart buttons.

FIGS. 21a and 21b show an embodiment of the main node 105 and of the power-supply unit 106.

In detail, as may be seen from the cross-section of FIG. 21b, the power-supply unit 106 is closed in a package 130, for example of plastic, and is housed in a pocket 133 of the garment 101 overlying the wired antenna 107 so that the embedded antenna 108 and the wired antenna 107 are magnetically coupled and the latter may receive power for supplying the entire network 100.

The wired antenna 107 of the power-supply unit 106 (like the wired antenna 110 of the smart buttons 104) may be obtained simply as a turn of conductive material for RF lines and antennas (such as, for example, a wire of aluminium or an aluminium alloy or coated with aluminium so as to prevent oxidation). The wired antenna 107 is formed by the same conductive wires as the electrical line 102 and is also integral with the fabric of the garment 101 similarly to what discussed previously with reference to FIGS. 20a and 20b, or the conductive wires may be sewn on a pre-existing fabric.

The pocket 133 may be a traditional pocket of the garment 101, or a purposely provided pocket, provided with a fastener (not shown), for example a zip or a Velcro® fastener that enables easy opening thereof for removal of the power-supply unit 106 together with the corresponding package 130, for example for replacing the battery 115 or for replacing the entire power-supply unit 106, when the battery 115 is run down.

FIG. 22a shows an embodiment where the wired antenna 107 is at least formed by a conductive wire 122, and a separate U-shaped portion of wire 124 is arranged between the forward stretch and the return stretch of the conductive wire 122 so as to form two fringing capacitors 134 in series to each other. In this way, the fringing capacitors 134 form, with the loop of the antenna 107, a parallel LC circuit forming a resonant antenna that enables a better transfer of energy from the power-supply unit 106 to the main node 105.

FIG. 22b shows a variant of FIG. 22a, where the fringing capacitor 134 is formed by two parallel stretches arranged close to the conductive wire 122.

Figure 23:
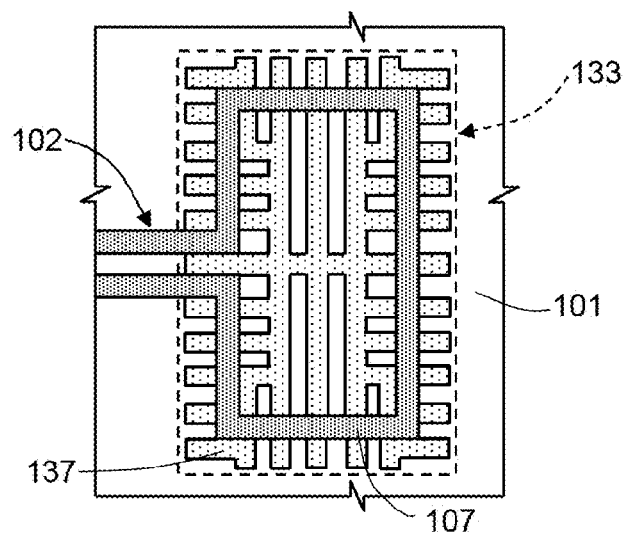
Figure 24:
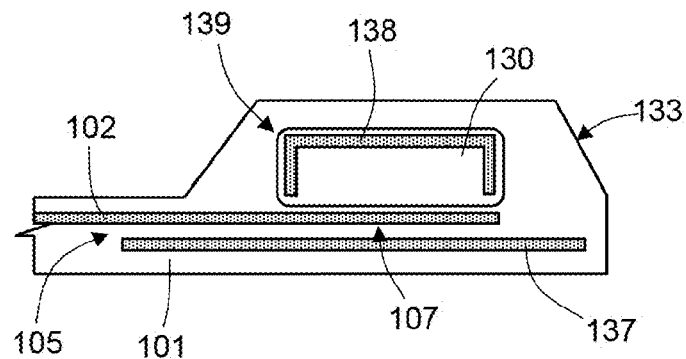
FIGS. 24 and 25 are two possible cross-sections of the detail of FIG. 23 according to an embodiment.

FIG. 23 shows an embodiment of the main node 105 wherein a magnetic shield 137 extends in the fabric of the garment 101 underneath the wired antenna 107 of the main node 105 (see also FIG. 24). The magnetic shield 137 is formed by a magnetic film, for example of a cobalt or nickel alloy or a soft magnetic material, with a different pattern, for example forming a regular or irregular plane geometry, such as a rectangle or square or a pattern formed by segments, coupled or not, the envelope whereof covers the entire area of the wired antenna 107.

The magnetic shield 137 enables shielding of the generated magnetic field for a person who is wearing the garment 101 and thus reduction of the dangerous effects in particular when the signals exchanged on the network 100 have a high frequency, for example of 1 GHz. In a variant, the magnetic shield may be replaced by a conductive shield, for example of aluminium.

Figure 25:
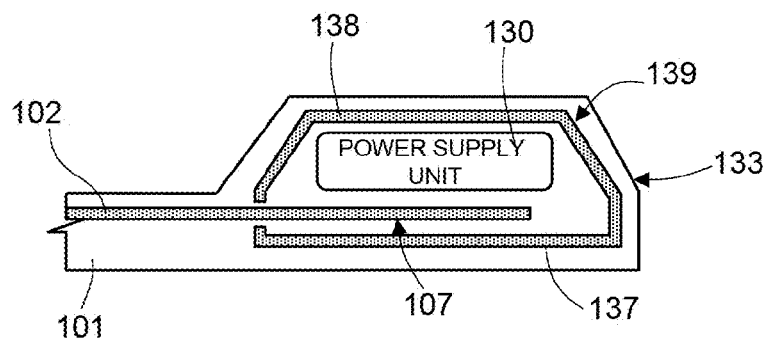

Moreover, the magnetic shield 137 may form part of a magnetic cage 139 also including a top portion 138, as shown in FIGS. 24 and 25 so as to obtain a good confinement of the magnetic field inside the pocket 133.

In FIG. 24, the top portion 138 of the magnetic cage 139 is formed within the package 130 of the power-supply unit 106 and also this is formed by a magnetic film, having a structure and made of materials similar to those of the magnetic shield 137, except for the fact that it extends spatially so as to define five surfaces of a polyhedron in an embodiment.

Alternatively, according to FIG. 25, the top portion 138 may be provided in the fabric of the pocket 103 and may be coupled or not to the magnetic shield 137. In either case, the magnetic cage 139 is electrically insulated from the conductive wires 122, 123.

Figure 26:
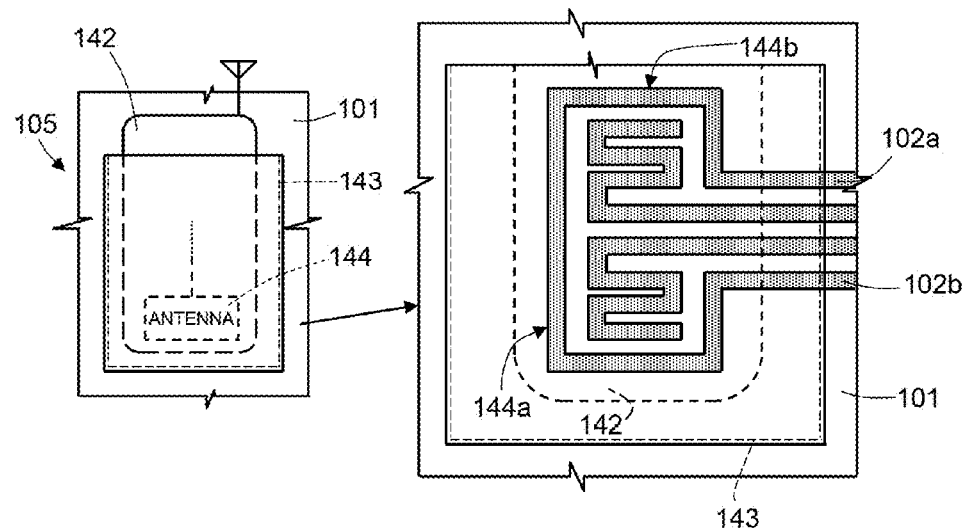
FIG. 26 is a top plan view of another detail of the network of FIG. 18 according to an embodiment.

FIG. 26 shows an embodiment wherein the main node 105 is coupled to a cell phone 142 that may be put in a pocket 143 of the garment 101, for example, a traditional pocket. Here, the cell phone 142 has an antenna 144 of an inductive type, similar to the embedded antennas 111 of the devices 104 or the embedded antenna 108 of the power-supply unit 106 and coupled to the wired antenna 107 arranged at the pocket 143. Alternatively, the antenna 144 may be formed by an antenna 144a of a Hertzian type (as shown in the enlarged detail of FIG. 26) and by an antenna 144b of an inductive type, coupled to the wired antenna 107 on the garment 101. The antenna 144b of the inductive type has the purpose of supplying energy, whereas the antenna 144a of the Hertzian type has an equivalent antenna (not shown and similar to the antenna 144a) on the garment 101 and may be used for communications.

With such an embodiment, the cell phone 142 operates as an interface between the network 100 and the outside world and is able, for example, to send signals outside, for example, measured vital parameters for medical analyses or alarm signals.

FIGS. 27a, 27b, and 28-30 show possible embodiments of the smart button, designated by 150, and of the corresponding wired antenna 110. Here, see FIG. 28, the smart button 150 has a structure similar to known press-studs and includes a mushroom-shaped body 151 and a fixing ring 152. The mushroom-shaped body 151 has a stem 153 and a head 154, and the fixing ring 152 has a hole 155 designed to house the terminal portion of the stem 153. To this end, the mushroom-shaped body 151 and the fixing ring 152 are made of partially compliant material, for example plastic, and have dimensions such as to generate an interference coupling and block the stem 153 safely inside the hole 155 (pressure blocking). Alternatively, the stem 153 may have a diameter slightly smaller than the hole 155 but have a peripheral projection co-operating with an annular groove of the fixing ring 152, or vice versa, so as to further ensure constant mutual positioning. Alternatively, other known fixing means may be provided, for example screw, magnet, or the like means.

The garment 101 is arranged between the head 154 and the fixing ring 152 and has, at the intermediate node 103, a through opening 160, passed by the stem 153. The through opening 160 has a diameter that is the same as or a little larger than the diameter of the stem 153. In addition, the head 154 of the mushroom-shaped body 151 and the fixing ring 152 are arranged on opposite sides of the garment 101.

Figure 27A:
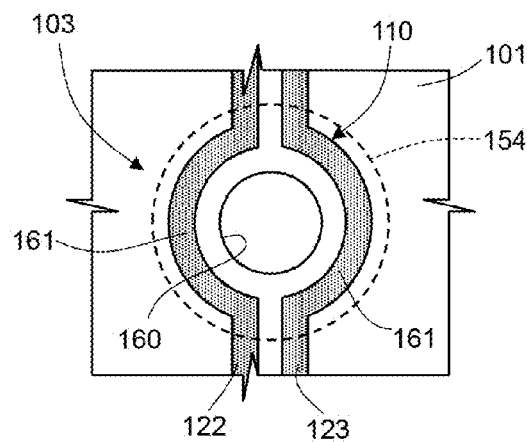
FIGS. 27a and 27b are top plan views of a different detail of the network of FIG. 18 according to an embodiment.

In the embodiment of FIG. 27a, within the garment 101, at the intermediate node 103, the conductive wires 122, 123 are curved to form semi-arched portions 161 surrounding the eyelet 160 on opposite sides so as to form a sort of loop forming the wired antenna 110.

Figure 27B:
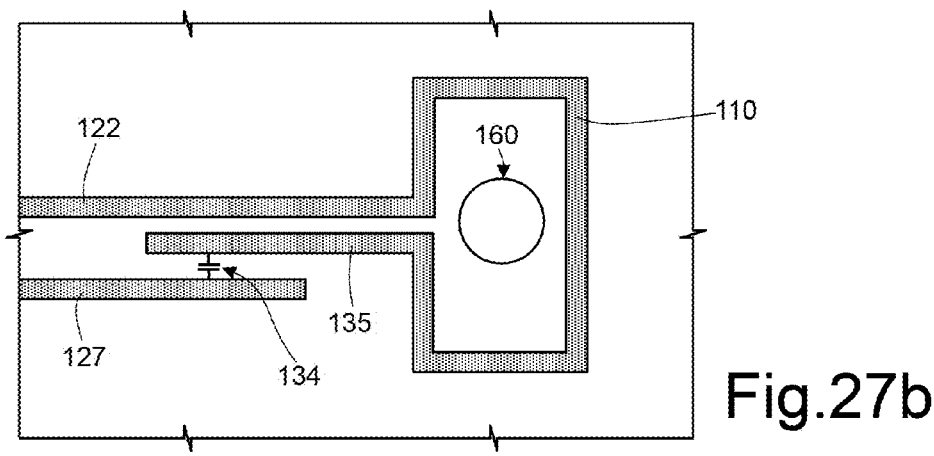

FIG. 27b shows an embodiment wherein the wired antenna 110 is formed by a first conductive wire 122 extending to form the loop of the wired antenna 110 and has a return portion 135 coupled to a second conductive wire 127 through a fringing capacitor 134. Here, the fringing capacitor 134 forms, with the loop 110, a series LC circuit of a resonant antenna that enables a better transfer of energy between the intermediate node 103 and the corresponding device 104.

In an embodiment, the fringing capacitor 134 of the series LC circuit reduces and in certain cases eliminates the need for welds or electrical couplings between the wires, in particular when the electrical line 102 and the corresponding plurality of nodes 103 are formed by a single conductive wire, as explained above.

Figure 28:
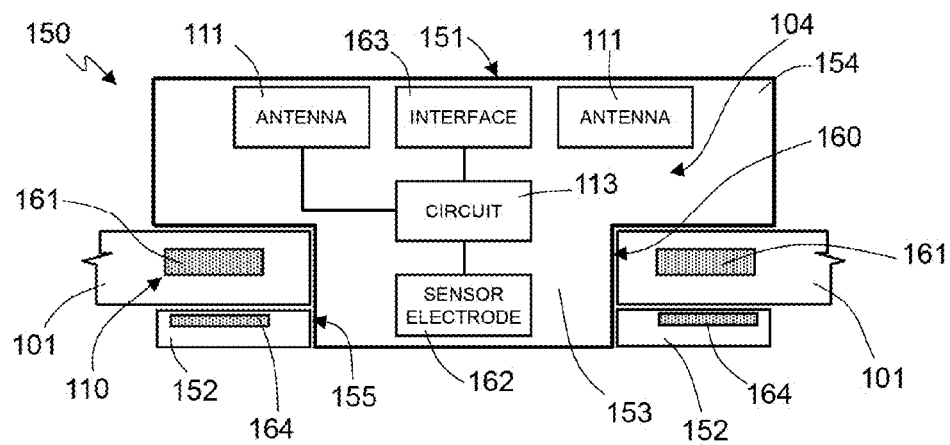
FIGS. 28-30 are cross-sections of embodiments of a detail complementary to the detail of FIG. 27.

As shown in FIG. 28, each mushroom-shaped body 151 houses a respective device 104; in detail, a functional element 112, here, for example, an electrode/sensor 162, is housed within the stem 153, while another functional element 112, for example an interface 163, is arranged in the head 154. The position and number of the functional elements 112 are only indicative and may vary according to the application. The interface 163 may include, for example, a LED element, a microphone, a loudspeaker, a switch, or a keypad membrane, for input of a datum.

The electronic circuit 113 is here housed in the head 154 and is coupled to the embedded antenna 111 and to the functional elements 112. Also here, the electronic circuit 113 may include an integrated circuit, a SoC, a SiP, or the like. In general, the functional element or elements 112 and the electronic circuit or circuits 113 may be arranged variously, according to the specific application. In addition, in a variant not shown, the embedded antenna 111 may be integrated within the electronic circuit 113.

In FIG. 28, two portions of the wired antenna 110 are shown, corresponding to the cross-section of the turn or turns forming wired antenna 110, and the fixing ring 152 contains a shield element 164 of an annular shape formed by a magnetic or conductive film, similar to the magnetic shield 137 of FIG. 24.

Figure 29:
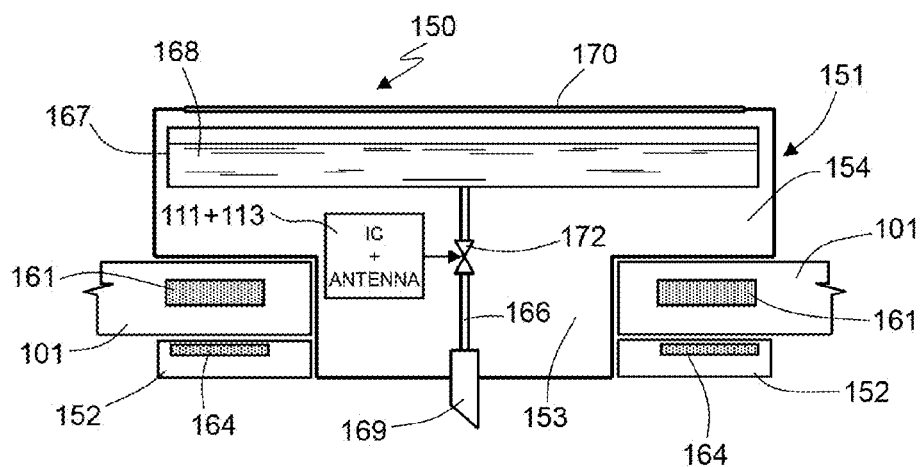

In an embodiment of FIG. 29, the functional elements 112 may include a container, tray, or vial 167 and a syringe 169 coupled together by a duct 166. In detail, here the container 167, filled with a medication 168 (for example insulin), is arranged, for example, in the head 154 and is coupled to the syringe 169, represented only schematically. The top surface of the head 154 is here formed by a transparent wall 170 for inspection of the container 167, for example in order to indicate when the latter is empty. The electronic circuit 113, here incorporating the embedded antenna 110, may regulate the passage of the medication 168 from the container 167 to the syringe 169, by controlling a valve 172 in the duct 166.

The smart button 150 of FIG. 29 may, for example, be a disposable component to be replaced after the container 167 has been emptied. Moreover, other smart buttons 150 of the network 100 may carry out monitoring of pre-set quantities (for example, the content of sugar in the blood of the person who is wearing the garment 101) in order to be able to dispense pre-set amounts of the medication 168 in a programmed way, when necessary.

Figure 30:
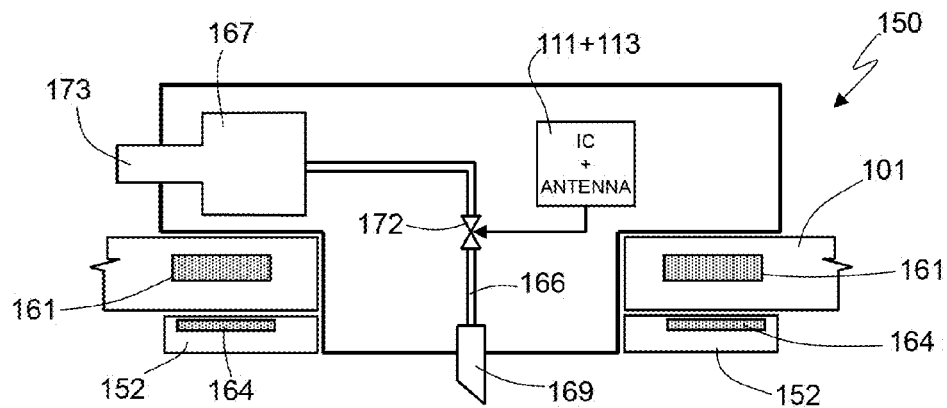

In FIG. 30, the container 167 is coupled to an input channel 173, one end whereof projects from the head 154. The input channel 173 has closing elements (not shown) or is coupled to an external reservoir (not shown) and enables filling of the container 167 when emptied.

Figure 31:
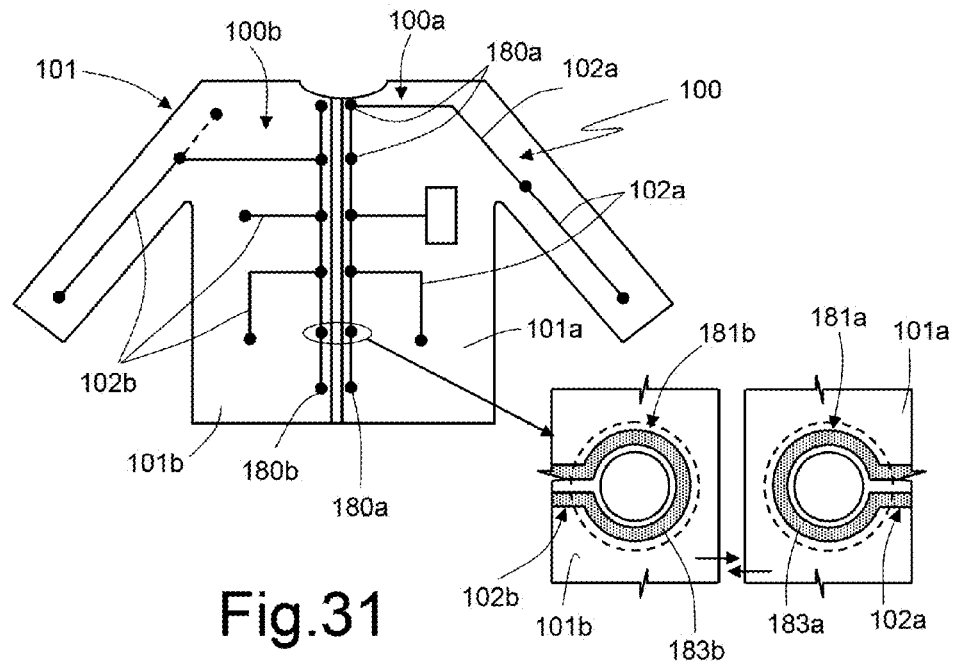
FIG. 31 shows a different embodiment of the present network, once again to be applied to a garment.

FIGS. 31-35 refer to an embodiment wherein the network 100 extends on various garments 101 or various parts of a same garment that are separated by a discontinuity, for example different flaps 101a, 101b of a jacket (as shown in FIG. 31), but may be coupled via buttons or some other closing system allowing overlapping of fabric flaps, if it is necessary to transfer power and thus a near-field magnetic coupling is required. In the alternative, the antennas could be close to one another if they are used only for communication, in which case it may be possible to use also far-field antennas (not shown).

In this case, the network 100 is formed by two or more network portions 100a and 100b, the electrical lines 102a, 102b whereof are not electrically coupled to one another because of at least one physically interrupted line.

According to FIG. 31, a single main node 105 supplies the network portions 100a and 100b. These have a plurality of end nodes 180a, 180b arranged at fastening elements (e.g., eyelets, buttons, press studs, zips), for example, in proximity of the edge of the respective flap 101a, 101b of the garment 101. In practice, the end nodes 180a and the end nodes 180b are equal in number and are arranged so that the overlapping of the two flaps 101a, 101b of a same garment 101 or of two different garments (not shown) and the possible fastening operation will lead to a superposition between each half-node 180a and a respective half-node 180b. The end nodes 180a, 180b are each basically formed by a respective loop antenna 183a, 183b embedded in the fabric of the garment 101. In this way, the operation of closing or fixing of the two flaps 101a, 101b leads to superposition of the loop antennas 183 and thus to magnetic coupling of the network portions 100a and 100b at the end nodes 180a, 180b (near-field coupling).

Consequently, in this case, the network 100 may include just one main node 105 and a just one power-supply unit 106.

Figure 32:
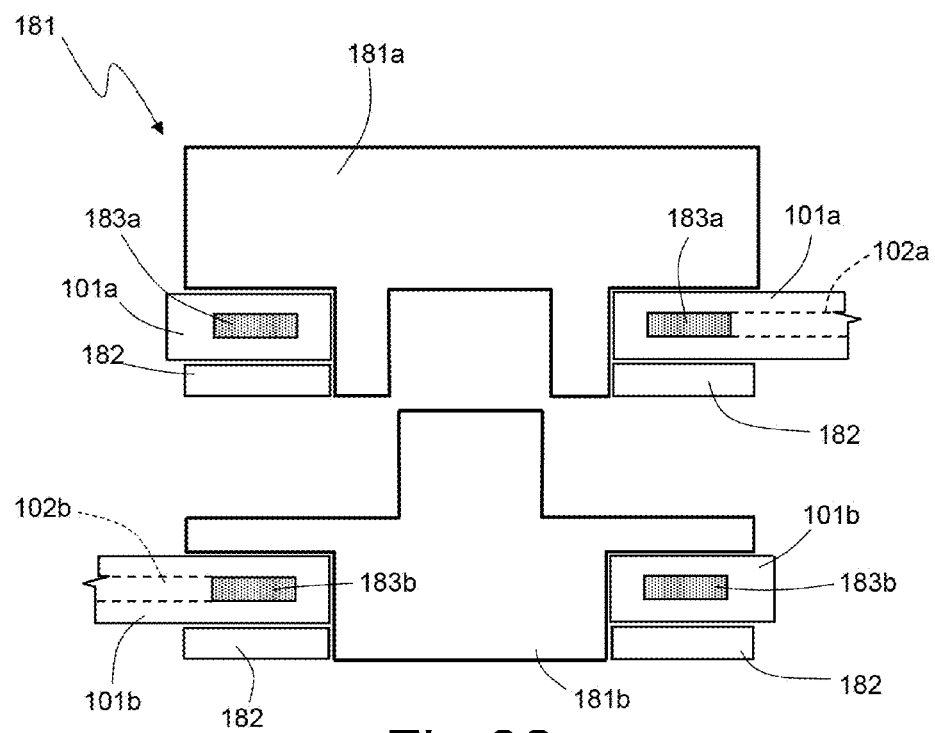
FIG. 32 shows a cross-section of the enlarged detail of the network of FIG. 31 according to an embodiment.

FIG. 32 shows the cross-section of the garment 101 when the garment 101 is fastened with fasteners 181 (e.g., snap fasteners, snaps, poppers, press-studs). In detail, the fasteners 181 are formed by two halves 181a, 181b similar to those of a traditional fastener, and are provided with blocking rings 182. Also here, the nodes 180a, 180b are formed within the fabric of the garment 101.

Alternatively, the fasteners 181 may provide an electrical coupling between the lines 102a, 102b of each half-network, exploiting the contiguity and direct contact between the two halves 181a, 181b of the fasteners 181. In this case, each fastener 181 may include couplers (formed by conductive portions fitted together) to create at least one electrical coupling. In this case, the antennas 183 may or may not be provided.

A device 104 may also be provided embedded in one of the two halves 181a, 181b of the fastener 181, which would thus operate as a smart button.

Figure 33A:
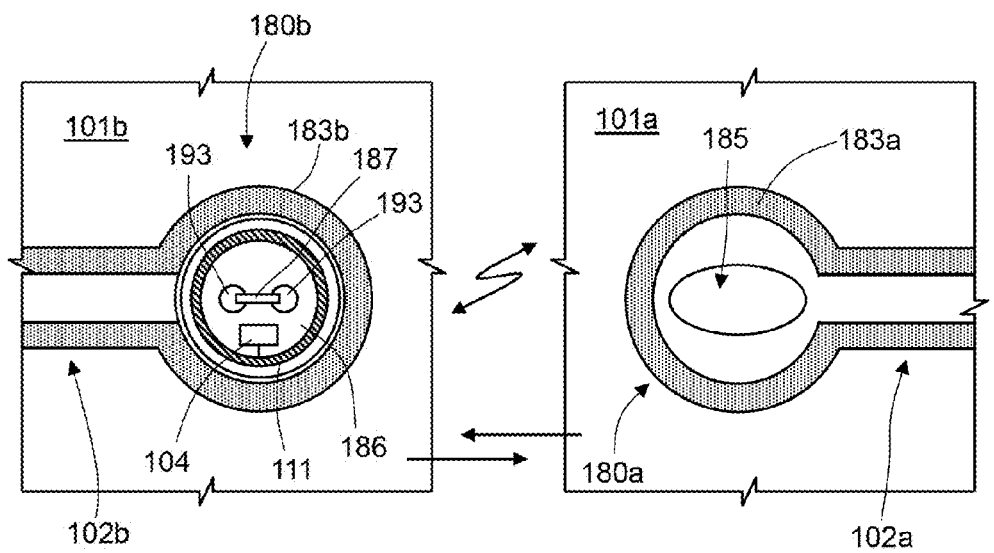
FIGS. 33a and 33b show in top plan view, in an unbuttoned condition, and in cross-section, in a buttoned condition, a different embodiment of the enlarged detail of the network of FIG. 31.
Figure 33B:
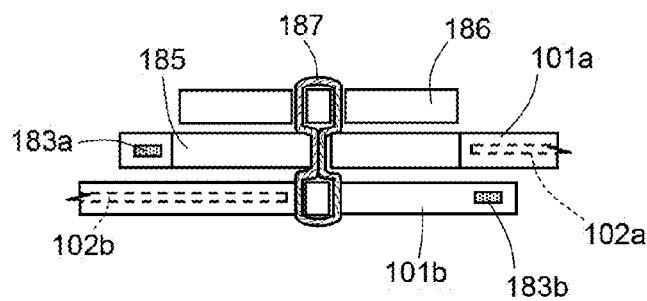

FIGS. 33a and 33b regard a garment 101 having a fastening system with button and eyelet. In this case, the end nodes 180a may be arranged at the eyelets 185, and the end nodes 180b may be provided at the buttons 186 of the type sewn using thread 187 on the respective flap of the garment 101.

Here, the end nodes 180a, 180b are once again formed each by a respective loop antenna 183a, 183b embedded or fixed in the respective flap of the garment 101 so that the operation of buttoning causes superposition of the loop antennas 183. The two loop antennas 183a, 183b have comparable dimensions. In addition, also here, the button 186 may embed a device 104 coupled, via the respective embedded antenna 110, to the underlying loop antennas 183. For example, the embedded antenna 110 of the device 104 may be arranged on the periphery of the button 186, for example formed on the top or bottom surface of the button 186.

Alternatively, the button 186 may embed the embedded antenna 110 of the device 104, and the loop antenna 183b of the half-node 180b may be formed in the respective flap of the garment 101b underneath the embedded antenna 110.

Figure 34:
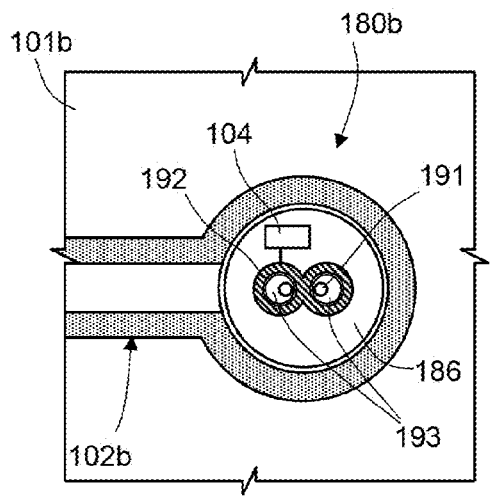
FIGS. 34-36 show another variant of the enlarged detail of the network of FIG. 31, respectively in top plan view and in cross-sectional view and of a single flap of the garment according to an embodiment.
Figure 35:
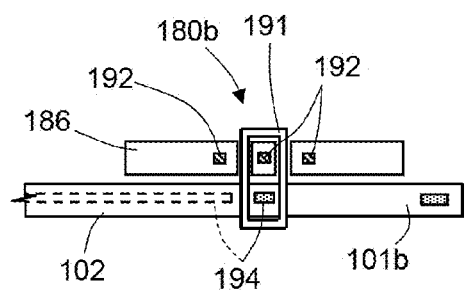
Figure 36:
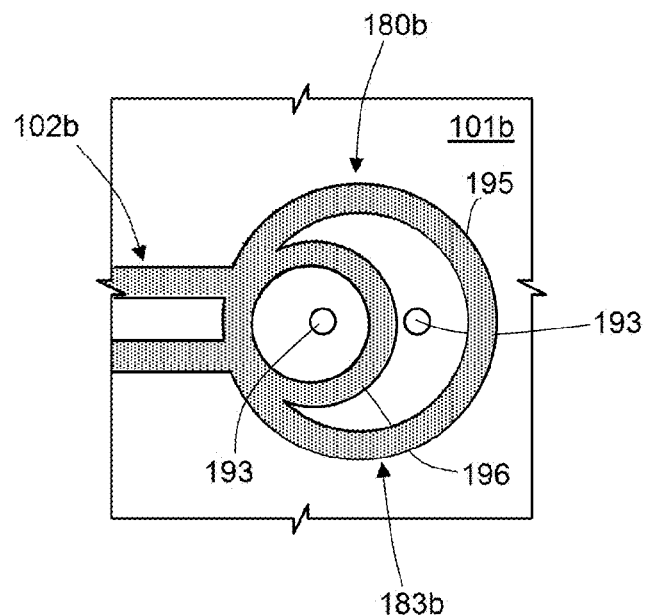

In FIGS. 34 and 35, a thread 191 that holds the button 186 attached to the respective flap 101b of the garment 101 is made of magnetic material. Here, the button 186 houses the antenna of the device 104, designated by 192 and arranged outside the device 104. The antenna 192 may have, for example, the shape of an 8 on its side so as to form two turns arranged alongside each other and contiguous, each surrounding a respective hole 193 of the button 186. The node 180b may here be formed by a similar double-loop antenna 194 with two turns (one whereof open, for coupling with the electrical line 102b), as may be seen in FIG. 36, where the button 186 has not been represented for clarity. Here, the loop antenna 183b forms two circumferences 195 and 196, whereof circumference 195 is external and is substantially congruent with, and superimposable (after buttoning) on, the loop antenna 183a on the other flap 101a, and circumference 196 is internal and passes between the holes 193 of the button 186 so as to couple with the antenna 192 of the device 104. Alternatively, the node 180b may be provided as a single turn arranged underneath one of the two turns of the double-loop antenna 192.

According to another alternative, the button 186 may not house any device 104, or the device 104 may have an own embedded antenna 111 as an alternative to the double-loop antenna 192.

The presence of the wire 191 of magnetic material enables an increase in the magnetic coupling between the two end nodes 180a, 180b and possibly the device 104.

Moreover, the external circumference 195 enables a good coupling with the loop antenna 183a on the other flap 101a, and the internal circumference 196 enables a good coupling with the double-loop antenna 192.

According to a variant not shown, the loop antenna 183b may be formed by a single turn, that passes between the holes 193 of the button 186 and has a circular or polygonal shape. Such an embodiment is particularly suitable if a button 186 has a double-loop antenna 192, as in FIG. 34.

Figure 37:
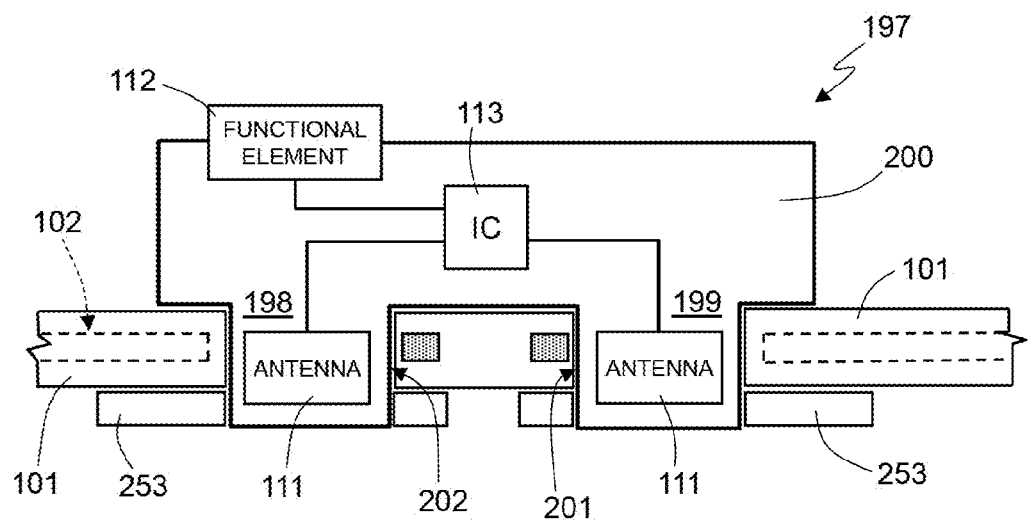
FIG. 37 shows a cross-sectional view of a different detail of the network of FIG. 31 according to an embodiment.
Figure 38:
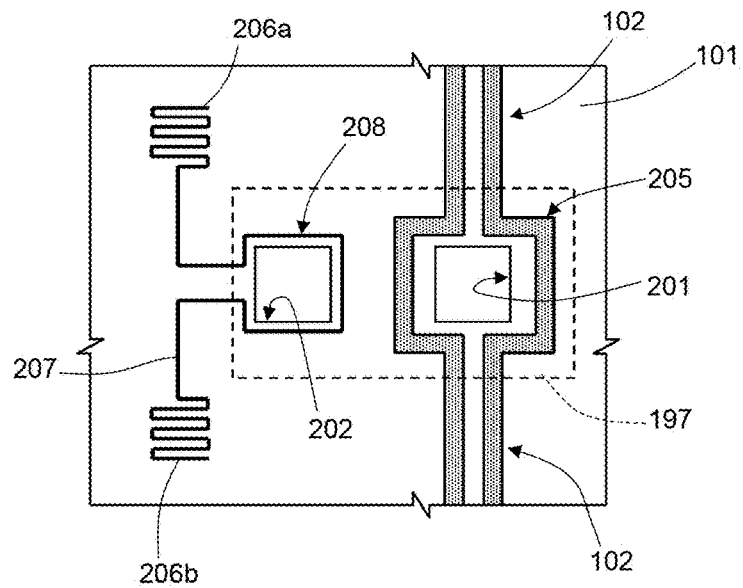
FIG. 38 is a top plan view of a detail complementary to that of FIG. 37 according to an embodiment.

FIGS. 37 and 38 show a smart button 197 that may be used for coupling two separate networks via a far-field coupling, for example the network 100 with a domotic network or a music installation, as represented by the dashed portion of the electrical line 102 of FIG. 31.

The smart button 197 has two stems 198, 199 projecting from a single head 200 and designed to extend each through a respective opening 201 and 202 of the garment 101. The stems 198, 199 are fixed through respective fixing rings 253, as has been described for the stem 153 of FIG. 28. Alternatively, a single fixing element may have two holes for fixing, coupling by snap-action, or coupling by interference with the stems 198, 199.

The smart button 197 houses one or more functional elements 112, one or more electronic circuits 113, and two embedded antennas 111, one for each stem 198, 199.

The garment 101 has a first wired antenna 205 surrounding one of the holes, here the hole 201, similarly to FIG. 27. The first wired antenna 205 is formed by the conductive wires 122, 123 and is magnetically coupled to one of the embedded antennas 111 of the smart button 197. In addition, the garment 101 has a Hertzian antenna formed by two dipoles 206a and 206b, coupled via electrical conductors 207 to a second wired antenna 208 extending around the other hole, here the hole 200, and coupled to the other embedded antenna 111 of the smart button 197.

Such an embodiment may be used in particular when the power-supply unit 106 does not have a far-field antenna.

Figure 39:
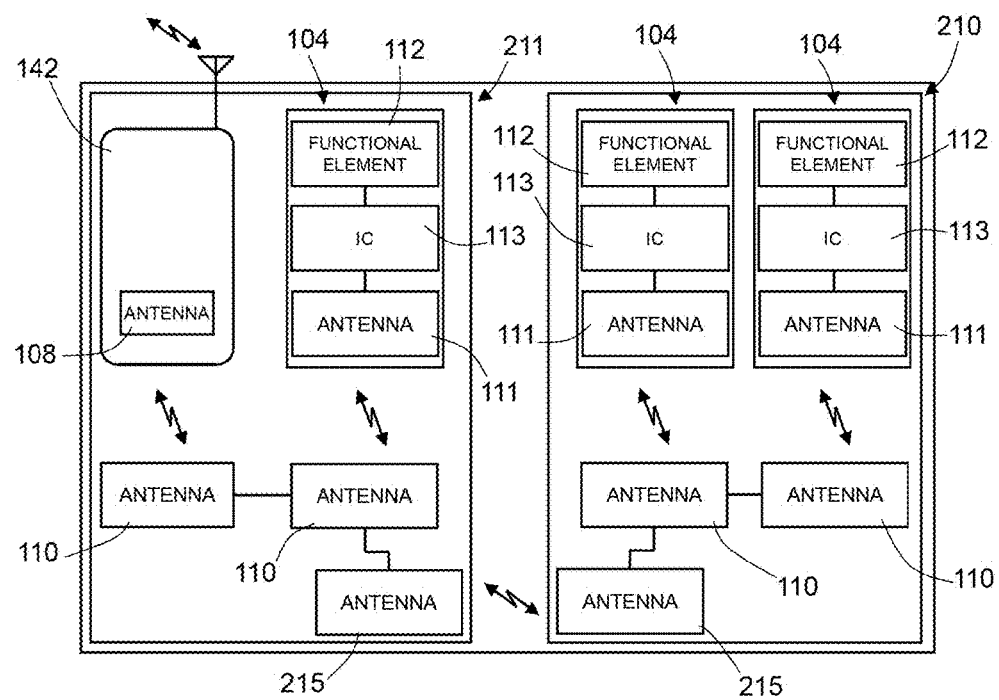
FIG. 39 is a block diagram of the coupling to two networks, once again for application to a garment or to two different garments according to an embodiment.

FIG. 39 shows an architecture that enables coupling between two different networks 210 and 211, each of which is formed as described for the network 100. The networks 210, 211 may be formed on a same garment 101 or on two adjacent garments, such as trousers and jacket of a pair of overalls. The two networks 210, 211 are coupled together through two antennas 215, in near field when there is a single power-supply unit 106 for the two networks 210, 211, for example arranged in the network 211. The two networks 210, 211 are coupled together through two far-field antennas 215, if both the networks have an own power-supply unit 106. One of the two networks, for example, the network 211, may be coupled to a cell phone 142 that enables coupling to the outside world; in this case, the cell phone 142 may also include the power-supply unit 106.

One of the two networks 210, 211 may be arranged also on an object different from a garment, for example on a watch bracelet, and may have a display for displaying signals generated by the sensors of the other network, without any power-supply unit, in so far as it receives the electrical power necessary for its operation from the other network.

The network described herein may have a number of advantages.

In fact, it may be formed on flexible supports and thus enables arrangement of electronic devices, which are in themselves not flexible, wherever necessary, since the coupling between the devices is obtained without contact (wireless), and thus folding of the support does not entail any risk of interrupting the electrical coupling.

In addition, it is modular, and may be easily adapted to the specific application by inserting or fixing devices suited for the purpose.

For example, in an embodiment of FIGS. 1-17, magnetic vias may traverse the devices 1 for improving coupling between the antennas 4 and the magnetic strips 17, moreover enabling use of a single strip that may possibly be closed to form a ring or toroid.

The individual embodiments described may be variously combined together so as to provide innumerable other embodiments, according to the application.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

The invention claimed is:

1. An article, comprising:
   a garment; and
   a network formed on the garment which comprises:
     a main node comprising a main wired antenna;
     at least one intermediate node comprising an intermediate wired antenna configured to be magnetically coupled to a respective electronic device for that intermediate node;
     an electrical line electrically coupling the main node to the at least one intermediate node;
     at least one electronic device magnetically coupled to the intermediate wired antenna; and
     a power supply unit magnetically coupled to the main node via the main wired antenna;
   wherein the main wired antenna comprises:
     a main conductive loop coupled to the electrical line and having a forward stretch and a return stretch formed on the garment;

a secondary conductive loop arranged between the forward stretch and the return stretch so as to form first and second fringing capacitors in series;

wherein the first and second fringing capacitors define, within the main conductive loop, a parallel LC circuit forming a resonant antenna facilitating transfer of energy from the power supply unit to the main node.

2. The article of claim 1, wherein the electrical line comprises a single conductive line; wherein the main wired antenna of the main node comprises a first bent end of the single conductive line; and wherein the intermediate wired antenna of the at least one intermediate node comprises a second bent end of the single conductive line.

3. The article of claim 1, wherein the power supply unit comprises a battery, a power inverter coupled to the battery and configured to generate AC voltage therefrom, and an antenna magnetically coupled to the main node and configured to transmit output from the power inverter to the main node.

4. The article of claim 3, wherein the power supply unit further comprises a memory unit coupled to the antenna of the power supply unit, the memory unit configured to receive data transmissions made from the intermediate wired antenna of the at least one intermediate node to the at least one electronic device, via the antenna of the power supply unit, and to store those data transmissions.

5. The article of claim 1, further comprising a far field antenna coupled to the electrical line, the far field antenna configured to enable coupling of the at least one electronic device to an external environment.

6. The article of claim 1, wherein the electrical line is embedded within fabric from which the garment is constructed.

7. The article of claim 1, wherein the garment, at least one electronic device, and power supply unit are galvanically insulated from one another.

8. The article of claim 1, wherein the garment has a pocket overlaying the main wired antenna; and wherein the power supply unit is carried within the pocket.

9. An article, comprising:
a garment; and
a network formed on the garment which comprises:
   a main node comprising a main wired antenna;
   at least one intermediate node comprising an intermediate wired antenna configured to be magnetically coupled to a respective electronic device for that intermediate node;
   an electrical line electrically coupling the main node to the at least one intermediate node;
   at least one electronic device magnetically coupled to the intermediate wired antenna; and
   a power supply unit magnetically coupled to the main node via the main wired antenna;
wherein the main wired antenna comprises:
   a main conductive loop coupled to the electrical line and having a forward stretch and a return stretch; and
   first and second parallel electrode stretches arranged adjacent to sides of the main conductive loop in a spaced apart manner therefrom to form a fringing capacitor;
   wherein the fringing capacitor defines, within the main conductive loop, a LC circuit forming a resonant antenna facilitating transfer of energy from the power supply unit to the main node.

10. The article of claim 9, wherein the electrical line comprises a single conductive line; wherein the main wired antenna of the main node comprises a first bent end of the single conductive line; and wherein the intermediate wired antenna of the at least one intermediate node comprises a second bent end of the single conductive line.

11. The article of claim 9, wherein the power supply unit comprises a battery, a power inverter coupled to the battery and configured to generate AC voltage therefrom, and an antenna magnetically coupled to the main node and configured to transmit output from the power inverter to the main node.

12. The article of claim 11, wherein the power supply unit further comprises a memory unit coupled to the antenna of the power supply unit, the memory unit configured to receive data transmissions made from the intermediate wired antenna of the at least one intermediate node to the at least one electronic device, via the antenna of the power supply unit, and to store those data transmissions.

13. The article of claim 9, further comprising a far field antenna coupled to the electrical line, the far field antenna configured to enable coupling of the at least one electronic device to an external environment.

14. The article of claim 9, wherein the electrical line is embedded within fabric from which the garment is constructed.

15. The article of claim 9, wherein the garment, at least one electronic device, and power supply unit are galvanically insulated from one another.

16. The article of claim 9, wherein the garment has a pocket overlaying the main wired antenna; and wherein the power supply unit is carried within the pocket.

17. An article, comprising:
a garment;
a network formed on the garment which comprises:
   a main node comprising a main wired antenna;
   at least one intermediate node comprising an intermediate wired antenna configured to be magnetically coupled to a respective electronic device for that intermediate node;
   an electrical line electrically coupling the main node to the at least one intermediate node;
   at least one electronic device magnetically coupled to the intermediate wired antenna; and
   a power supply unit magnetically coupled to the main node via the main wired antenna; and
a magnetic cage over and partially surrounding the main wired antenna so the magnetic cage serves to shield a wearer of the garment from a magnetic field about the main wired antenna; wherein a first surface of the magnetic cage is carried within the power supply unit; and wherein the magnetic cage is electrically insulated from the main wired antenna and the power supply unit.

18. The article of claim 17, wherein the magnetic cage is polyhedral in shape.

19. The article of claim 17, further comprising a shield carried within the garment adjacent to, aligned with, and under the main wired antenna so the shield serves to shield a wearer of the garment from a magnetic field about the main wired antenna.

20. The article of claim 17, wherein the power supply unit includes a portable housing carrying components of the power supply unit; and wherein at least a portion of the magnetic cage is carried within the portable housing of the power supply unit.

21. The article of claim 17, wherein the electrical line comprises a single conductive line; wherein the main wired antenna of the main node comprises a first bent end of the single conductive line; and wherein the intermediate wired antenna of the at least one intermediate node comprises a second bent end of the single conductive line.

22. The article of claim 17, wherein the power supply unit comprises a battery, a power inverter coupled to the battery and configured to generate AC voltage therefrom, and an antenna magnetically coupled to the main node and configured to transmit output from the power inverter to the main node.

23. The article of claim 22, wherein the power supply unit further comprises a memory unit coupled to the antenna of the power supply unit, the memory unit configured to receive data transmissions made from the intermediate wired antenna of the at least one intermediate node to the at least one electronic device, via the antenna of the power supply unit, and to store those data transmissions.

24. The article of claim 17, further comprising a far field antenna coupled to the electrical line, the far field antenna configured to enable coupling of the at least one electronic device to an external environment.

25. The article of claim 17, wherein the electrical line is embedded within fabric from which the garment is constructed.

26. The article of claim 17, wherein the garment, at least one electronic device, and power supply unit are galvanically insulated from one another.

27. The article of claim 17, wherein the garment has a pocket overlaying the main wired antenna; and wherein the power supply unit is carried within the pocket.

* * * * *